(12) United States Patent
Pfluecker et al.

(10) Patent No.: US 8,758,501 B2
(45) Date of Patent: Jun. 24, 2014

(54) NANOPARTICULATE UV PROTECTANT WITH SILICON DIOXIDE COATING

(75) Inventors: Frank Pfluecker, Darmstadt (DE); Bernd Hirthe, Toenisvorst (DE); Heike Saenger, Moers (DE); Stephan John, Duisburg (DE)

(73) Assignees: Merck Patent GmbH, Darmstadt (DE); Sachtleben Chemie GmbH, Duisburg (DE)

( * ) Notice: Subject to any disclaimer, the term of this patent is extended or adjusted under 35 U.S.C. 154(b) by 266 days.

(21) Appl. No.: 12/432,949

(22) Filed: Apr. 30, 2009

(65) Prior Publication Data

US 2009/0220441 A1    Sep. 3, 2009

Related U.S. Application Data

(63) Continuation of application No. 10/565,214, filed as application No. PCT/EP2004/007311 on Jan. 20, 2006, now abandoned.

(30) Foreign Application Priority Data

Jul. 21, 2003 (DE) .................................. 103 33 029

(51) Int. Cl.
    *B05D 7/00* (2006.01)
(52) U.S. Cl.
    USPC ............... 106/482; 106/3; 106/286; 106/287; 424/59
(58) Field of Classification Search
    USPC .................. 106/482, 286, 437, 425; 428/404
    See application file for complete search history.

(56) References Cited

U.S. PATENT DOCUMENTS

| | | | |
|---|---|---|---|
| 5,180,585 A * | 1/1993 | Jacobson et al. | 424/405 |
| 5,268,337 A | 12/1993 | Katz et al. | |
| 5,776,239 A * | 7/1998 | Bruno | 106/437 |
| 6,235,270 B1 | 5/2001 | Ishii et al. | |
| 6,395,081 B1 | 5/2002 | Hiew et al. | |
| 6,500,415 B2 | 12/2002 | Ishii et al. | |
| 6,773,814 B2 * | 8/2004 | Schumacher et al. | 428/404 |
| 2002/0017221 A1 | 2/2002 | Hamor et al. | |
| 2002/0041853 A1 | 4/2002 | Ishii et al. | |
| 2002/0165308 A1 | 11/2002 | Kinniard et al. | |
| 2003/0104198 A1 | 6/2003 | Schumacher et al. | |
| 2006/0210500 A1 | 9/2006 | Bicard-Benhamou et al. | |

FOREIGN PATENT DOCUMENTS

| | | | |
|---|---|---|---|
| EP | 0 393 857 A1 | | 10/1990 |
| EP | 0576188 A1 | | 6/1993 |
| EP | 0675086 | * | 4/1996 |
| EP | 0675086 | * | 10/1996 |
| EP | 0 748 624 A1 | | 12/1996 |
| EP | 0 988 853 A | | 3/2000 |
| EP | 1 284 277 A | | 2/2003 |
| EP | 1 287 807 A | | 3/2003 |
| JP | 0675086 | * | 10/1996 |
| JP | 11-256133 | | 9/1999 |
| JP | 11-302015 | | 11/1999 |
| WO | WO 94/04131 A1 | | 3/1994 |
| WO | WO 02/068544 A | | 9/2002 |
| WO | WO 2004/056927 A2 | | 7/2004 |

OTHER PUBLICATIONS

English Machine Translation from the Japanese Patent Office for JP-11-256133; Publication Date: Sep. 21, 1999.
English Machine Translation from the Japanese Patent Office for JP-11-302015; Publication Date: Nov. 2, 1999.

* cited by examiner

*Primary Examiner* — Melvin C Mayes
*Assistant Examiner* — Colette Nguyen
(74) *Attorney, Agent, or Firm* — Millen, White, Zelano & Branigan, P.C.

(57) ABSTRACT

The present invention relates to nanoparticulate UV protectants which are obtainable by hydrothermal treatment of a nanoparticulate metal oxide and subsequent application of a silicon dioxide coating, and to the preparation and use thereof. The present invention furthermore relates to novel compositions, in particular for topical application, which are intended, in particular, for light protection of the skin and/or of the hair against UV radiation, and to the use thereof in the above-mentioned cosmetic application.

19 Claims, 4 Drawing Sheets

NANOPARTICULATE UV PROTECTANT WITH SILICON DIOXIDE COATING

This application is a continuation application of U.S. application Ser. No. 10/565,214, filed on Jan. 20, 2006 now abandoned.

The present invention relates to nanoparticulate UV protectants, to the preparation and use thereof. The present invention furthermore relates to novel compositions for topical application which are intended, in particular, for light protection of the skin and/or the hair against UV radiation (compositions which are referred to below simply as sunscreen compositions), and to the use thereof in the above-mentioned cosmetic application.

It is known that the human epidermis can be tanned by light radiation having a wavelength in the range from 280 to 400 nm and that radiation having a wavelength in the range from 280 to 320 nm, which is known under the term UV-B, causes erythema and skin burning, which may be detrimental to the formation of a natural tan. The UV-B radiation should therefore be filtered out.

It is furthermore known that UV-A radiation having a wavelength in the range from 320 to 400 nm, which tans the skin, can cause a change in the skin, in particular in the case of sensitive skin or skin which is exposed continuously to sunlight. UV-A radiation causes, in particular, a loss in skin elasticity and wrinkling, which results in premature ageing. It favours the triggering of erythema formation or increases this reaction in some people, and it can even be the cause of toxic or allergic reactions triggered by light. It is therefore desirable also to filter out the UV-A radiation.

In cosmetics, numerous organic sunscreen filters which are able to absorb the harmful UV-A radiation more or less selectively have been indicated to date.

A group of UV-A filters which is particularly interesting in this respect currently consists of dibenzoylmethane derivatives, in particular 4,4'-methoxy-tert-butyldibenzoylmethane, which have a strong intrinsic absorption capacity. These dibenzoylmethane derivatives, which are currently well-known products per se as filters which are effective in the UV-A region, are described, in particular, in the French patent applications FR-A-2 326 405 and FR-A-2 440 933 and in European patent application EP-A-0 114 607. 4,4'-Methoxy-tert-butyldibenzoylmethane is in addition currently commercially available from Merck under the trade name Eusolex® 9020.

These dibenzoylmethane derivatives can be combined with a UV-B filter in order to obtain complete protection over the entire spectrum of sunlight in the UV region.

It is furthermore known that the addition of an inorganic pigment and in particular of a titanium dioxide ($TiO_2$) pigment enables the light-protection properties of sunscreen compositions comprising UV filters to be improved.

The combination of dibenzoylmethane derivatives and nanoparticulate metal oxides of metal oxides is therefore highly regarded in the area of sunscreen compositions.

However, it is found that the combinations of dibenzoylmethane derivatives and inorganic nanoparticulate metal oxides and in particular the combination of 4,4'-methoxy-tert-butyldibenzoylmethane and metal oxides has a number of disadvantages which have an effect not only on the type and thus the quality of the products containing them, but also on their attractiveness to the consumers. On the one hand, increased degradation of dibenzoylmethane derivatives in formulations is frequently observed if titanium dioxide particles are present in the compositions comprising this type of combination On the other hand, difficulties repeatedly arise in cosmetic formulations comprising this combination due to complexes of the dibenzoylmethane derivative crystallising out. Furthermore, a colour change which is perceived in a more or less intense yellow or red coloration of the formulations is frequently observed. Apart from the fact that this phenomenon reduces the light-protection capacity of the dibenzoylmethane derivatives and in particular of 4,4'-methoxy-tert-butyldibenzoylmethane, this coloration is of course undesired from a cosmetic point of view.

It is furthermore observed that these phenomena are particularly pronounced in the case of $TiO_2$ nanopigments.

Various attempts to solve some of these problems have already been indicated in the prior art: Japanese patent application JP61-215314 recommended the use of masking agents selected from edetic acid, metaphosphoric acid, polyphosphoric acid and/or the salts of these acids in order to reduce the phenomenon of the yellow coloration. However, this solution is not entirely satisfactory.

It is observed in European Patent Application EP-A-0 748 624 that the use of nanoparticulate metal oxides of titanium dioxide which have been treated with a silicone (silane derivative or siloxane derivative) significantly reduces the yellow coloration which is usually observed in the sunscreen compositions comprising conventional combinations of the dibenzoylmethane derivatives/$TiO_2$ pigment type.

Furthermore, the specification WO-A-94/04131 discloses light-stable filter compositions which comprise a dibenzoylmethane derivative in combination with a benzylidenecamphor derivative in well-defined proportions. According to this specification, the dibenzoylmethane derivative can be stabilised to light by the benzylidenecamphor in the stated proportions, i.e. its decomposition under the action of UV radiation and in particular UV-A radiation can be restricted. It is stated in the same specification that these photostable compositions may furthermore comprise an organic pigment which blocks UV radiation and in particular a titanium dioxide pigment, which may be coated with a compound and in particular with a silicone-containing compound.

In spite of these attempts to solve the above-mentioned problems on combination of dibenzoylmethane derivatives with metal-oxide particles, there is still a demand for a metal-oxide grade which simultaneously solves all the said problems in a satisfactory manner.

Surprisingly, it has now been found that it is possible to employ certain nanoparticulate UV protectants which have a silicon dioxide coating in cosmetic formulations comprising dibenzoylmethane derivatives and at the same time to solve the said problems in a satisfactory manner.

The present invention firstly relates to a nanoparticulate UV protectant which has a silicon dioxide coating which is obtainable by hydrothermal treatment of a nanoparticulate metal oxide and subsequent application of a silicon dioxide coating.

Hydrothermal treatment is taken to mean the heating of an aqueous solution or suspension or dispersion in a closed container, optionally under pressure (cf. also Ullmanns Enzyklopädie der Technischen Chemie [Ullmann's Encyclopaedia of Industrial Chemistry], 4th Edition, 1978, Volume 15, pp. 117 ff: K. Recker, The Growing of Single Crystals).

For the purposes of the present invention, a nanoparticulate UV protectant is preferably taken to mean a nanoparticulate metal oxide with silicon dioxide coating. The crystallite size of the nanoparticulate metal oxide in the nanoparticulate UV protectant, determined by the Scherrer method, is usually in the range from 5 nm to 100 nm, preferably in the range from 8 to 50 nm and particularly preferably below 25 nm. The dimensions of the nanoparticulate metal oxide, which can be determined in a transmission electron microscope, are usually at a length of 5 to 150 nm and a width of 5 to 60 nm. The length is preferably in the range from 20 to 60 nm and the width in the range from 8 to 30 nm.

The nanoparticulate metal oxides used here for the use according to the invention are, in particular, titanium dioxide, iron oxides, zinc oxide or also cerium oxides, where titanium dioxide is particularly preferred in accordance with the invention as metal oxide since it achieves the objects according to the invention in a particular manner. Titanium dioxide can be in rutile or anatase form or in amorphous form, but preferably in rutile and/or anatase form here. The preferred primary particle size is in the range from 5 to 50 nm. The primary particles here, in particular in the case of anatase, are preferably round, while rutile primary particles frequently occur in needle or spindle form right up to ovals ("egg-shaped"). However, round rutile primary particles can also be employed in accordance with the invention.

The silicon dioxide coating should cover the nanoparticulate metal oxide as completely as possible and, since it is, however, inert as UV filter, should nevertheless not be present in excessive amounts. It has been found that it is advantageous for the silicon dioxide content, based on the nanoparticulate UV protectant as a whole, to be 5 to 50% by weight, preferably 8 to 30% by weight and particularly preferably 12 to 20% by weight.

The resultant nanoparticulate UV protectant usually exhibits a particle size determined by the Scherrer method in the range from 5 nm to 100 nm, preferably in the range from 8 to 50 nm and particularly preferably below 25 nm. The dimensions of the nanoparticulate UV protectant, which can be determined in a transmission electron microscope, are usually at a length of 5 to 160 nm and a width of 10 to 70 nm. The length is preferably in the range from 30 to 70 nm and the width in the range from 18 to 40 nm.

The nanoparticulate UV protectant according to the invention exhibits advantageous properties here compared with the prior art with respect to:

UV absorption, in particular broad-band or UV-B absorption,
transparency in visible light (VIS),
good, in particular increased photostability,
reduced or inhibited photoactivity,
hydrophilic surface, good incorporation and settling stability in aqueous phases;
silica surface, which can, if desired, easily be hydrophobically modified using known techniques,
ready dispersibility in aqueous and oily phases,
in combination with dibenzoylmethane derivatives, in particular:
  reduced discoloration of the formulation and/or
  diminishing discoloration of the formulation during storage and/or
  no or reduced crystallisation of complexes of the dibenzoylmethane derivatives and/or
  increased storage stability of the dibenzoylmethane derivatives and/or
  improved light-protection action, in particular after storage,
in combination with self-tanning agents, in particular dihydroxyacetone, reduced destabilisation of the self-tanning agent compared with the prior art, or none at all, is observed,
in combination with benzophenone derivatives, in particular 2-hydroxy-4-methoxybenzophenone, stabilisation of the benzophenone derivatives is observed.

It has been found here, in particular, that it may be advantageous for simultaneous realisation of the above-mentioned advantages if the nanoparticulate metal oxide is doped with cerium or iron, preferably iron.

In another, likewise preferred variant of the present invention, however, the nanoparticulate metal oxide is free from dopants.

The diminishing discoloration of the formulation during storage on combination with dibenzoylmethane derivatives is evident at all usual storage temperatures for cosmetic formulations, in particular at 4° C., room temperature and 50° C. This positive effect begins immediately after preparation of the formulation. Re-intensification of the discoloration does not occur—if known to date—in the usual service life of a cosmetic formulation.

As already mentioned above, the nanoparticulate UV protectants having the properties according to the invention are obtained, for example, if a certain preparation process is observed.

Correspondingly, the present invention furthermore relates to a process for the preparation of a nanoparticulate metal oxide having light-protection properties which is characterised in that a) a nanoparticulate metal oxide is subjected to hydrothermal treatment and
b) a silicon dioxide coating is subsequently applied.

As already stated above, it may be preferred in this process for the nanoparticulate metal oxide employed in step a) to be a nanoparticulate titanium dioxide, which may preferably be doped with iron.

The hydrothermal treatment here is preferably carried out at temperatures in the range from 40 to 360° C., preferably in the range from 80 to 220° C. and particularly preferably in the range from 140 to 200° C.

The hydrothermal treatment results in the formation of stable nanocrystallites of uniform size and shape. At low temperatures, "needle-shaped" crystallites form. With increasing temperature, the crystallites become rounded. Oval shapes form which become round particles at very high temperatures. In addition, uniform crystal growth occurs, which results in a reduction in the reactivity and photoactivity.

Advantages of the hydrothermal treatment compared with a conventional thermal treatment (heat treatment of a dried powder) are:

formation of uniform crystallite sizes with a narrow particle-size distribution
prevention of sintering effects (formation of undesired aggregates)

The silicon dioxide coating in step b) is preferably carried out as a sol-gel process, in which a water-glass solution is particularly preferably added to a suspension of the metal oxide.

In an advantageous variant of the present invention, the sol-gel process here is carried out with the pH kept constant. The pH kept constant can be in a range from pH 2 to pH 11, with the pH preferably being in the range from pH=5 to pH=8, particularly preferably in the range from pH=6 to pH=7.

A further advantageous variant of the present invention is addition of all of the water-glass necessary for the post-treatment at a pH=7 to pH=11 without keeping the pH constant. The pH is subsequently lowered to a value of pH=5 to pH=8, preferably to pH=6 to pH=7.

It is furthermore preferred for step b) to be carried out at elevated temperature, preferably at a temperature in the range from 50° C. to 110° C.

In all the said variants of the process according to the invention, a maturing time after the coating is complete is advantageous. The maturing time should be between 1 h and 8 h, preferably 2 h to 4 h, and should be carried out at a temperature of 50° C. to 110° C.

It may furthermore be advantageous with respect to the agglomerate sizes desired during later processing for the product subsequently to be ground. The conventional grinding techniques which can be used for nanoparticulate materials can be employed here.

Owing to the above-mentioned advantages, the present invention furthermore relates to a composition having light-protection properties which comprises at least one nanoparticulate UV protectant according to the invention.

In a variant of the invention, the compositions are preferably compositions which can be applied topically, for example cosmetic or dermatological formulations. The compositions in this case comprise a cosmetically or dermatologically suitable carrier and, depending on the desired property profile, optionally further suitable ingredients.

Further compositions which are preferred in accordance with the invention are selected from the group consisting of fibres, textiles, including coatings thereof, paints, coating systems, films and packaging for the protection of foods, plants or industrial products.

Accordingly, the present invention furthermore relates to the use of a nanoparticulate UV protectant according to the invention or of a nanoparticulate UV protectant prepared by a process according to the invention for incorporation into paints, coating systems, films, packaging, fibres, textiles and rubber or silicone rubber mouldings, such as tyres or insulators.

Besides the advantages already mentioned above, the use of the nanoparticulate UV protectants according to the invention in compositions which are emulsions can, in particular, also contribute towards stabilisation of the emulsion. In general, this can reduce the use of emulsifiers or, in an individual case (Pickering emulsion), even obviate the use of emulsifiers entirely. Preference is therefore also given in accordance with the invention to emulsifier-free emulsions which comprise the nanoparticulate UV protectants according to the invention.

Preferred compositions having light-protection properties comprise at least one dibenzoylmethane derivative. The dibenzoylmethane derivatives used for the purposes of the present invention are, as already indicated, products which are already well known per se and which are described, in particular, in the above-mentioned specifications FR-A-2 326 405, FR-A-2 440 933 and EP-A-0 114 607. The dibenzoylmethane derivatives which can be used in accordance with the invention can be selected, in particular, from the dibenzoylmethane derivatives of the following formula:

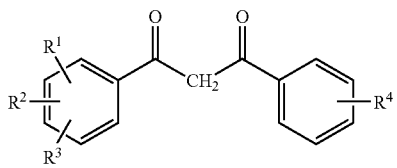

in which $R^1$, $R^2$, $R^3$ and $R^4$, which are identical or different from one another, denote hydrogen, a straight-chain or branched $C_{1-8}$-alkyl group or a straight-chain or branched $C_{1-8}$-alkoxy group. In accordance with the present invention, it is of course possible to use one dibenzoylmethane derivative or a plurality of dibenzoylmethane derivatives. Of the dibenzoylmethane derivatives to which the present invention specifically relates, mention may be made, in particular, of:
2-methyldibenzoylmethane,
4-methyldibenzoylmethane,
4-isopropyldibenzoylmethane,
4-tert-butyldibenzoylmethane,
2,4-dimethyldibenzoylmethane,
2,5-dimethyldibenzoylmethane,
4,4'-diisopropyldibenzoylmethane,
4,4'-methoxy-tert-butyldibenzoylmethane,
2-methyl-5-isopropyl-4'-methoxydibenzoylmethane,
2-methyl-5-tert-butyl-4'-methoxydibenzoylmethane,
2,4-dimethyl-4'-methoxydibenzoylmethane
and
2,6-dimethyl-4-tert-butyl-4'-methoxydibenzoylmethane,
this list being non-restrictive.

Of the above-mentioned dibenzoylmethane derivatives, particular preference is given in accordance with the invention to 4,4'-methoxy-tert-butyldibenzoylmethane and especially 4,4'-methoxy-tert-butyldibenzoylmethane, which is commercially available under the trade name Eusolex® 9020 from Merck, this filter conforming to the following structural formula:

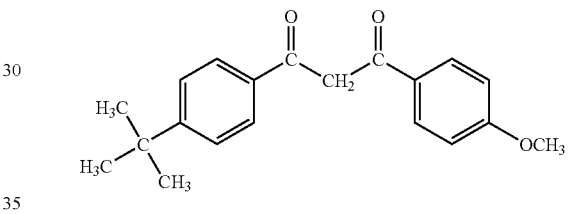

A further dibenzoylmethane derivative which is preferred in accordance with the invention is 4-isopropyldibenzoylmethane.

Further preferred compositions having light-protection properties comprise at least one benzophenone or benzophenone derivative, such as, particularly preferably, 2-hydroxy-4-methoxybenzophenone (for example Eusolex® 4360) or 2-hydroxy-4-methoxybenzophenone-5-sulfonic acid and the sodium salt thereof (for example Uvinul® MS-40).

The dibenzoylmethane derivative(s) or the benzophenone derivative(s) may be present in the compositions according to the invention in proportions which are generally in the range from 0.1 to 10% by weight and preferably in proportions which are in the range from 0.3 to 5% by weight, where these proportions are based on the total weight of the composition.

Owing to the above-mentioned advantages, the present invention furthermore also relates to the use of a nanoparticulate metal oxide having light-protection properties according to the invention for the stabilisation of UV filters, in particular dibenzoylmethane and dibenzoylmethane derivatives or benzophenone and benzophenone derivatives.

It may furthermore be preferred in accordance with the invention for the compositions to comprise further inorganic UV filters. Preference is given here both to those from the group consisting of titanium dioxides, such as, for example, coated titanium dioxide (for example Eusolex® T-2000, Eusolex® T-AQUA), zinc oxides (for example Sachtotec®), iron oxides, also cerium oxides. These inorganic UV filters are generally incorporated into cosmetic compositions in an amount of 0.5 to 20 percent by weight, preferably 2-10%. In particular, it may be preferred here for a nanoparticulate UV protectant according to the invention to be present in one phase in emulsions and a further inorganic UV filter to be present in the other phase.

In a further, likewise preferred embodiment of the present invention, the composition according to the invention comprises at least one self-tanning agent.

Advantageous self-tanning agents which can be employed are, inter alia:

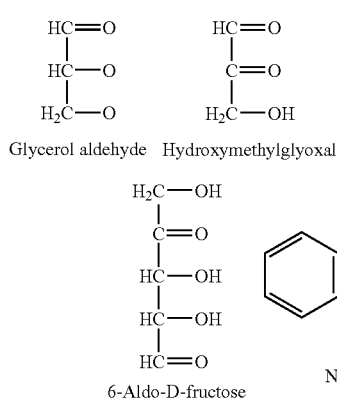

Glycerol aldehyde   Hydroxymethylglyoxal   γ-Dialdehyde   Erythrulose

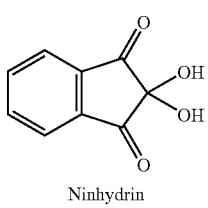

6-Aldo-D-fructose   Ninhydrin

Mention should also be made of 5-hydroxy-1,4-naphthoquinone (juglone), which is extracted from the shells of fresh walnuts

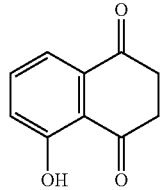

5-Hydroxy-1,4-naphthoquinone (juglone)

and 2-hydroxy-1,4-naphthoquinone (lawsone), which occurs in henna leaves.

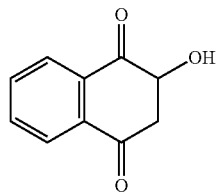

2-Hydroxy-1,4-naphthoquinone (lawsone)

Very particular preference is given to 1,3-dihydroxyacetone (DHA), a trifunctional sugar which occurs in the human body, and derivatives thereof.

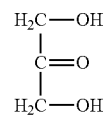

1,3-Dihydroxyacetone (DHA)

The present invention furthermore relates to the use of a nanoparticulate UV protectant according to the invention for the stabilisation of self-tanning agents, in particular dihydroxyacetone or dihydroxyacetone derivatives.

Furthermore, the compositions according to the invention may also comprise dyes and coloured pigments. The dyes and coloured pigments can be selected from the corresponding positive list in the German Cosmetics Regulation or the EC list of cosmetic colorants. In most cases, they are identical with the dyes approved for foods. Advantageous coloured pigments are, for example, titanium dioxide, mica, iron oxides (for example $Fe_2O_3$, $Fe_3O_4$, $FeO(OH)$) and/or tin oxide. Advantageous dyes are, for example, carmine, Berlin Blue, Chromium Oxide Green, Ultramarine Blue and/or Manganese Violet. It is particularly advantageous to select the dyes and/or coloured pigments from the following list. The Colour Index numbers (CINs) are taken from the Rowe Colour Index, 3rd Edition, Society of Dyers and Colourists, Bradford, England, 1971.

| Chemical or other name | CIN | Colour |
| --- | --- | --- |
| Pigment Green | 10006 | Green |
| Acid Green 1 | 10020 | Green |
| 2,4-Dinitrohydroxynaphthalene-7-sulfonic acid | 10316 | Yellow |
| Pigment Yellow 1 | 11680 | Yellow |
| Pigment Yellow 3 | 11710 | Yellow |
| Pigment Orange 1 | 11725 | Orange |
| 2,4-Dihydroxyazobenzene | 11920 | Orange |
| Solvent Red 3 | 12010 | Red |
| 1-(2'-Chloro-4'-nitro-1'-phenylazo)-2-hydroxynaphthalene | 12085 | Red |
| Pigment Red 3 | 12120 | Red |
| Ceres Red; Sudan Red; Fat Red G | 12150 | Red |
| Pigment Red 112 | 12370 | Red |
| Pigment Red 7 | 12420 | Red |
| Pigment Brown 1 | 12480 | Brown |
| 4-(2'-Methoxy-5'-sulfodiethylamido-1'-phenylazo)-3-hydroxy-5''-chloro-2'',4''-dimethoxy-2-naphthanilide | 12490 | Red |
| Disperse Yellow 16 | 12700 | Yellow |
| 1-(4-Sulfo-1-phenylazo)-4-aminobenzene-5-sulfonic acid | 13015 | Yellow |
| 2,4-Dihydroxyazobenzene-4'-sulfonic acid | 14270 | Orange |
| 2-(2,4-Dimethylphenylazo-5-sulfonyl)-1-hydroxynaphthalene-4-sulfonic acid | 14700 | Red |
| 2-(4-Sulfo-1-naphthylazo)-1-naphthol-4-sulfonic acid | 14720 | Red |
| 2-(6-Sulfo-2,4-xylylazo)-1-naphthol-5-sulfonic acid | 14815 | Red |
| 1-(4'-Sulfophenylazo)-2-hydroxynaphthalene | 15510 | Orange |

-continued

| Chemical or other name | CIN | Colour |
|---|---|---|
| 1-(2-Sulfonyl-4-chloro-5-carboxy-1-phenylazo)-2-hydroxy-naphthalene | 15525 | Red |
| 1-(3-Methylphenylazo-4-sulfonyl)-2-hydroxynaphthalene | 15580 | Red |
| 1-(4',(8')-Sulfonylnaphthylazo)-2-hydroxynaphthalene | 15620 | Red |
| 2-Hydroxy-1,2'-azonaphthalene-1'-sulfonic acid | 15630 | Red |
| 3-Hydroxy-4-phenylazo-2-naphthylcarboxylic acid | 15800 | Red |
| 1-(2-Sulfo-4-methyl-1-phenylazo)-2-naphthylcarboxylic acid | 15850 | Red |
| 1-(2-Sulfo-4-methyl-5-chloro-1-phenylazo)-2-hydroxy-naphthalene-3-carboxylic acid | 15865 | Red |
| 1-(2-Sulfo-1-naphthylazo)-2-hydroxynaphthalene-3-carboxylic acid | 15880 | Red |
| 1-(3-Sulfo-1-phenylazo)-2-naphthol-6-sulfonic acid | 15980 | Orange |
| 1-(4-Sulfo-1-phenylazo)-2-naphthol-6-sulfonic acid | 15985 | Yellow |
| Allura Red | 16035 | Red |
| 1-(4-Sulfo-1-naphthylazo)-2-naphthol-3,6-disulfonic acid | 16185 | Red |
| Acid Orange 10 | 16230 | Orange |
| 1-(4-Sulfo-1-naphthylazo)-2-naphthol-6,8-disulfonic acid | 16255 | Red |
| 1-(4-Sulfo-1-naphthylazo)-2-naphthol-3,6,8-trisulfonic acid | 16290 | Red |
| 8-Amino-2-phenylazo-1-naphthol-3,6-disulfonic acid | 17200 | Red |
| Acid Red 1 | 18050 | Red |
| Acid Red 155 | 18130 | Red |
| Acid Yellow 121 | 18690 | Yellow |
| Acid Red 180 | 18736 | Red |
| Acid Yellow 11 | 18820 | Yellow |
| Acid Yellow 17 | 18965 | Yellow |
| 4-(4-Sulfo-1-phenylazo)-1-(4-sulfophenyl)-5-hydroxy-pyrazolone-3-carboxylic acid | 19140 | Yellow |
| Pigment Yellow 16 | 20040 | Yellow |
| 2,6-(4'-Sulfo-2'',4''-dimethyl)bisphenylazo)-1,3-dihydroxy-benzene | 20170 | Orange |
| Acid Black 1 | 20470 | Black |
| Pigment Yellow 13 | 21100 | Yellow |
| Pigment Yellow 83 | 21108 | Yellow |
| Solvent Yellow | 21230 | Yellow |
| Acid Red 163 | 24790 | Red |
| Acid Red 73 | 27290 | Red |
| 2-[4''-(4''-Sulfo-1''-phenylazo)-7'-sulfo-1'-naphthylazo]-1-hydroxy-7-aminonaphthalene-3,6-disulfonic acid | 27755 | Black |
| 4-[4''-Sulfo-1''-phenylazo)-7'-sulfo-1'-naphthylazo]-1-hydroxy-8-acetylaminonaphthalene-3,5-disulfonic acid | 28440 | Black |
| Direct Orange 34, 39, 44, 46, 60 | 40215 | Orange |
| Food Yellow | 40800 | Orange |
| trans-β-Apo-8'-carotene aldehyde (C$_{30}$) | 40820 | Orange |
| trans-Apo-8'-carotinic acid (C$_{30}$) ethyl ester | 40850 | Orange |
| Canthaxanthine | 40850 | Orange |
| Acid Blue 1 | 42045 | Blue |
| 2,4-Disulfo-5-hydroxy-4'-4''-bis(diethylamino)triphenylcarbinol | 42051 | Blue |
| 4-[(4-N-Ethyl-p-sulfobenzylamino)-phenyl-(4-hydroxy-2-sulfo-phenyl)(methylene)-1-(N-ethyl-N-p-sulfobenzyl)-2,5-cyclo-hexadienimine] | 42053 | Green |
| Acid Blue 7 | 42080 | Blue |
| (N-Ethyl-p-sulfobenzylamino)phenyl-(2-sulfophenyl)methylene-(N-ethyl-N-p-sulfobenzyl)-Δ$^{2,5}$-cyclohexadienimine | 42090 | Blue |
| Acid Green 9 | 42100 | Green |
| Diethyldisulfobenzyldi-4-amino-2-chlorodi-2-methylfuchsonimmonium | 42170 | Green |
| Basic Violet 14 | 42510 | Violet |
| Basic Violet 2 | 42520 | Violet |
| 2'-Methyl-4'-(N-ethyl-N-m-sulfobenzyl)amino-4''-(N-diethyl)-amino-2-methyl-N-ethyl-N-m-sulfobenzylfuchsonimmonium | 42735 | Blue |
| 4'-(N-Dimethyl)amino-4''-(N-phenyl)aminonaphtho-N-dimethylfuchsonimmonium | 44045 | Blue |
| 2-Hydroxy-3,6-disulfo-4,4'-bisdimethylaminonaphthofuchsonimmonium | 44090 | Green |
| Acid Red 52 | 45100 | Red |
| 3-(2'-Methylphenylamino)-6-(2'-methyl-4'-sulfophenylamino)-9-(2''-carboxyphenyl)xanthenium salt | 45190 | Violet |
| Acid Red 50 | 45220 | Red |
| Phenyl-2-oxyfluorone-2-carboxylic acid | 45350 | Yellow |
| 4,5-Dibromofluorescein | 45370 | Orange |
| 2,4,5,7-Tetrabromofluorescein | 45380 | Red |
| Solvent Dye | 45396 | Orange |
| Acid Red 98 | 45405 | Red |
| 3',4',5',6'-Tetrachloro-2,4,5,7-tetrabromofluorescein | 45410 | Red |
| 4,5-Diiodofluorescein | 45425 | Red |
| 2,4,5,7-Tetraiodofluorescein | 45430 | Red |
| Quinophthalone | 47000 | Yellow |
| Quinophthalonedisulfonic acid | 47005 | Yellow |
| Acid Violet 50 | 50325 | Violet |

-continued

| Chemical or other name | CIN | Colour |
|---|---|---|
| Acid Black 2 | 50420 | Black |
| Pigment Violet 23 | 51319 | Violet |
| 1,2-Dioxyanthraquinone, calcium-aluminium complex | 58000 | Red |
| 3-Oxypyrene-5.8.10-sulfonic acid | 59040 | Green |
| 1-Hydroxy-4-N-phenylaminoanthraquinone | 60724 | Violet |
| 1-Hydroxy-4-(4'-methylphenylamino)anthraquinone | 60725 | Violet |
| Acid Violet 23 | 60730 | Violet |
| 1,4-Di(4'-methylphenylamino)anthraquinone | 61565 | Green |
| 1,4-Bis(o-sulfo-p-toluidino)anthraquinone | 61570 | Green |
| Acid Blue 80 | 61585 | Blue |
| Acid Blue 62 | 62045 | Blue |
| N,N'-Dihydro-1,2,1',2'-anthraquinonazine | 69800 | Blue |
| Vat Blue 6; Pigment Blue 64 | 69825 | Blue |
| Vat Orange 7 | 71105 | Orange |
| Indigo | 73000 | Blue |
| Indigodisulfonic acid | 73015 | Blue |
| 4,4'-Dimethyl-6,6'-dichlorothioindigo | 73360 | Red |
| 5,5'-Dichloro-7,7'-dimethylthioindigo | 73385 | Violet |
| Quinacridone Violet 19 | 73900 | Violet |
| Pigment Red 122 | 73915 | Red |
| Pigment Blue 16 | 74100 | Blue |
| Phthalocyanine | 74160 | Blue |
| Direct Blue 86 | 74180 | Blue |
| Chlorinated phthalocyanine | 74260 | Green |
| Natural Yellow 6, 19; Natural Red 1 | 75100 | Yellow |
| Bixin, Nor-Bixin | 75120 | Orange |
| Lycopene | 75125 | Yellow |
| trans-alpha-, -beta- or -gamma-Carotene | 75130 | Orange |
| Keto and/or hydroxyl derivatives of carotene | 75135 | Yellow |
| Guanine or pearlescent agent | 75170 | White |
| 1,7-Bis(4-hydroxy-3-methoxyphenyl)-1,6-heptadiene-3,5-dione | 75300 | Yellow |
| Complex salt (Na, Al, Ca) of carminic acid | 75470 | Red |
| Chlorophyll a and b; copper compounds of chlorophylls and chlorophyllines | 75810 | Green |
| Aluminium | 77000 | White |
| Aluminium hydroxide | 77002 | White |
| Water-containing aluminium silicates | 77004 | White |
| Ultramarine | 77007 | Blue |
| Pigment Red 101 and 102 | 77015 | Red |
| Barium sulfate | 77120 | White |
| Bismuth oxychloride and mixtures thereof with mica | 77163 | White |
| Calcium carbonate | 77220 | White |
| Calcium sulfate | 77231 | White |
| Carbon | 77266 | Black |
| Pigment Black 9 | 77267 | Black |
| Carbo medicinalis vegetabilis | 77268:1 | Black |
| Chromium oxide | 77288 | Green |
| Chromium oxide, water-containing | 77278 | Green |
| Pigment Blue 28, Pigment Green 14 | 77346 | Green |
| Pigment Metal 2 | 77400 | Brown |
| Gold | 77480 | Brown |
| Iron oxides and hydroxides | 77489 | Orange |
| Iron oxide | 77491 | Red |
| Iron oxide hydrate | 77492 | Yellow |
| Iron oxide | 77499 | Black |
| Mixtures of iron(II) and iron(III) hexacyanoferrate | 77510 | Blue |
| Pigment White 18 | 77713 | White |
| Manganese ammonium diphosphate | 77742 | Violet |
| Manganese phosphate; $Mn_3(PO_4)_2 \cdot 7\ H_2O$ | 77745 | Red |
| Silver | 77820 | White |
| Titanium dioxide and mixtures thereof with mica | 77891 | White |
| Zinc oxide | 77947 | White |
| 6,7-Dimethyl-9-(1'-D-ribityl)isoalloxazine, lactoflavin | | Yellow |
| Sugar dye | | Brown |
| Capsanthin, capsorubin | | Orange |
| Betanin | | Red |
| Benzopyrylium salts, anthocyans | | Red |
| Aluminium, zinc, magnesium and calcium stearate | | White |
| Bromothymol Blue | | Blue |

It may furthermore be favourable to select, as dye, one or more substances from the following group: 2,4-dihydroxyazobenzene, 1-(2'-chloro-4'-nitro-1'-phenylazo)-2-hydroxynaphthalene, Ceres Red, 2-(4-sulfo-1-naphthylazo)-1-naphthol-4-sulfonic acid, the calcium salt of 2-hydroxy-1,2'-azonaphthalene-1'-sulfonic acid, the calcium and barium salts of 1-(2-sulfo-4-methyl-1-phenylazo)-2-naphthylcarboxylic acid, the calcium salt of 1-(2-sulfo-1-naphthylazo)-2-hydroxynaphthalene-3-carboxylic acid, the aluminium salt of 1-(4-sulfo-1-phenylazo)-2-naphthol-6-sulfonic acid, the aluminium salt of 1-(4-sulfo-1-naphthylazo)-2-naphthol-3,6-disulfonic acid, 1-(4-sulfo-1- naphthylazo)-2-naphthol-6,8-disulfonic acid, the aluminium salt of 4-(4-sulfo-1-phenylazo)-2-(4-sulfophenyl)-5-hydroxypyrazolone-3-carboxylic acid, the aluminium and zirconium salts of 4,5-dibromofluorescein, the aluminium and zirconium salts of 2,4,5,7-tetrabromofluorescein, 3',4',5',6'-tetrachloro-2,4,5,7-tetrabromofluorescein and its aluminium salt, the aluminium salt of 2,4,5,7-tetraiodofluorescein, the aluminium salt of quinophthalonedisulfonic acid, the aluminium salt of indigodisulfonic acid, red and black iron oxide (GIN: 77491 (red) and 77 499 (black)), iron oxide hydrate (CIN: 77492), manganese ammonium diphosphate and titanium dioxide.

Also advantageous are oil-soluble natural dyes, such as, for example, paprika extract, β-carotene or cochineal.

Also advantageous for the purposes of the present invention are gel creams comprising pearlescent pigments. Particular preference is given to the types of pearlescent pigment listed below:
1. Natural pearlescent pigments, such as, for example,
    "pearl essence" (guanine/hypoxanthine mixed crystals from fish scales) and
    "mother-of-pearl" (ground mussel shells)
2. Monocrystalline pearlescent pigments, such as, for example, bismuth oxychloride (BiOCl)
3. Layered substrate pigments: for example mica/metal oxide The basis for pearlescent pigments is formed by, for example, pulverulent pigments or castor oil dispersions of bismuth oxychloride and/or titanium dioxide as well as bismuth oxychloride and/or titanium dioxide on mica. The lustre pigment listed under CIN 77163, for example, is particularly advantageous.

Also advantageous are, for example, the following pearlescent pigment types based on mica/metal oxide:

| Group | Coating/layer thickness | Colour |
| --- | --- | --- |
| Silver-white pearlescent pigments | $TiO_2$: 40-60 nm | silver |
| Interference pigments | $TiO_2$: 60-80 nm | yellow |
|  | $TiO_2$: 80-100 nm | red |
|  | $TiO_2$: 100-140 nm | blue |
|  | $TiO_2$: 120-160 nm | green |
| Coloured lustre pigments | $Fe_2O_3$ | bronze |
|  | $Fe_2O_3$ | copper |
|  | $Fe_2O_3$ | red |
|  | $Fe_2O_3$ | red-violet |
|  | $Fe_2O_3$ | red-green |
|  | $Fe_2O_3$ | black |
| Combination pigments | $TiO_2/Fe_2O_3$ | gold shades |
|  | $TiO_2/Cr_2O_3$ | green |
|  | $TiO_2$/Berlin Blue | dark blue |

Particular preference is given to, for example, the pearlescent pigments available from Merck under the trade names Timiron, Colorona or Dichrona.

The list of the said pearlescent pigments is of course not intended to be limiting. Pearlescent pigments which are advantageous for the purposes of the present invention can be obtained by numerous routes known per se. For example, other substrates apart from mica can also be coated with further metal oxides, such as, for example, silica and the like. For example, $TiO_2$- and $Fe_2O_3$-coated $SiO_2$ particles ("Ronasphere" grades), which are marketed by Merck and are particularly suitable for the optical reduction of fine wrinkles, are advantageous.

It may additionally be advantageous to completely omit a substrate such as mica. Particular preference is given to pearlescent pigments prepared using $SiO_2$. Such pigments, which may additionally also have goniochromatic effects, are available, for example, from BASF under the trade name Sicopearl Fantastico.

It may also be advantageous to employ Engelhard/Mearl pigments based on calcium sodium borosilicate coated with titanium dioxide. These are available under the name Reflecks. Due to their particle size of 40-80 μm, they have a glitter effect in addition to the colour.

Also particularly advantageous are effect pigments available from Flora Tech under the trade name Metasomes Standard/Glitter in various colours (yellow, red, green, blue). The glitter particles here are in the form of mixtures with various assistants and dyes (such as, for example, the dyes with the colour index (CI) numbers 19140, 77007, 77289, 77491).

The dyes and pigments can be in individual form or in the form of a mixture and mutually coated with one another, with different colour effects generally being caused by different coating thicknesses. The total amount of dyes and colouring pigments is advantageously selected from the range from, for example, 0.1% by weight to 30% by weight, preferably from 0.5 to 15% by weight, in particular from 1.0 to 10% by weight, in each case based on the total weight of the compositions.

In accordance with the invention, the nanoparticulate UV protectants may also be provided with a surface treatment which strengthens the hydrophilic or hydrophobic properties. Suitable for hydrophobic modification is, for example, a silicone or silane coating.

The silicones are, as is known, organosilicon polymers or oligomers having a straight-chain or cyclic, branched or crosslinked structure with various molecular weights which are obtained by polymerisation and/or polycondensation of suitably functionalised silanes and are essentially formed from recurring main units in which the silicon atoms are linked to one another via oxygen atoms (siloxane bond), where optionally substituted hydrocarbon groups are bonded directly to the silicon atoms via a carbon atom. The commonest hydrocarbon groups are the alkyl groups and in particular methyl, the fluoroalkyl groups, the aryl groups and in particular phenyl and the alkenyl groups and in particular vinyl. Further types of group which can be bonded to the siloxane chain either directly or via a hydrocarbon group are, in particular, hydrogen, the halogens and in particular chlorine, bromine or fluorine, the thiols, the alkoxy groups, the polyoxyalkylene groups (or polyethers) and in particular polyoxyethylene and/or polyoxypropylene, hydroxyl groups or hydroxyalkyl groups, the optionally substituted amino groups, the amide groups, the acyloxy groups or acyloxyalkyl groups, the hydroxyalkyl-amino groups or aminoalkyl groups, quaternary ammonium groups, amphoteric groups or betaine groups, anionic groups, such as carboxylates, thioglycolates, sulfosuccinates, thiosulfates, phosphates and sulfates, where this list is of course in no way limiting (so-called 'organo-modified' silicones).

For the purposes of the present invention, the term 'silicones' is also intended to encompass and cover the silanes and in particular the alkylsilanes required for their preparation.

The silicones which are suitable for the present invention, which can be used for sheathing the nanoparticulate UV protectants, are preferably selected from the alkylsilanes, the polydialkylsiloxanes and the polyalkylhydrogenosiloxanes. The silicones are more preferably selected from octyltrimethylsilane, the polydimethylsiloxanes and the polymethylhydrogenosiloxanes.

The nanoparticulate UV protectants can be present in the compositions according to the invention in proportions which are generally in the range from 0.1 to 50% by weight and preferably in proportions which are in the range from 0.5 to 20% by weight, where these proportions are based on the total weight of the composition.

The sunscreen compositions according to the invention may of course comprise one or more additional hydrophilic or lipophilic sunscreen filters which are effective in the UV-A region and/or UV-B region and/or IR and/or VIS region (absorbers). These additional filters can be selected, in particular, from cinnamic acid derivatives, salicylic acid derivatives, camphor derivatives, triazine derivatives, β,β-diphenyl acrylate derivatives, p-aminobenzoic acid derivatives and polymeric filters and silicone filters, which are described in the application WO 93/04665. Further examples of organic filters are indicated in patent application EP-A 0 487 404.

In principle, all UV filters are suitable for combination with the nanoparticulate UV protectants according to the invention. Particular preference is given to UV filters whose physiological acceptability has already been demonstrated. Both for UVA and UVB filters, there are many proven substances which are known from the specialist literature, for example benzylidenecamphor derivatives, such as 3-(4'-methylbenzylidene)-dl-camphor (for example Eusolex® 6300), 3-benzylidenecamphor (for example Mexoryl® SD), polymers of N-{(2 and 4)-[(2-oxoborn-3-ylidene)methyl] benzyl}acrylamide (for example Mexoryl® SW), N,N,N-trimethyl-4-(2-oxoborn-3-ylidenemethyl)anilinium methylsulfate (for example Mexoryl® SK) or (2-oxoborn-3-ylidene) toluene-4-sulfonic acid (for example Mexoryl® SL), methoxycinnamic acid esters, such as octyl methoxycinnamate (for example Eusolex® 2292), isopentyl 4-methoxycinnamate, for example as a mixture of the isomers (for example Neo Heliopan® E 1000), salicylate derivatives, such as 2-ethylhexyl salicylate (for example Eusolex® OS), 4-isopropylbenzyl salicylate (for example Megasol®) or 3,3,5-trimethylcyclohexyl salicylate (for example Eusolex® HMS), 4-aminobenzoic acid and derivatives, such as 4-aminobenzoic acid, 2-ethylhexyl 4-(dimethylamino)benzoate (for example Eusolex® 6007), ethoxylated ethyl 4-aminobenzoate (for example Uvinul® P25), phenylbenzimidazolesulfonic acids, such as 2-phenylbenzimidazole-5-sulfonic acid and the potassium, sodium and triethanolamine salts thereof (for example Eusolex® 232), 2,2-(1,4-phenylene)bisbenzimidazole-4,6-disulfonic acid and salts thereof (for example Neoheliopan® AP) or 2,2-(1, 4-phenylene)bisbenzimidazole-6-sulfonic acid;

and further substances, such as 2-ethylhexyl 2-cyano-3,3-diphenylacrylate (for example Eusolex® OCR), 3,3'-(1,4-phenylenedimethylene)bis(7,7-dimethyl-2-oxobicyclo[2.2.1]hept-1-yl-methanesulfonic acid and salts thereof (for example Mexoryl® SX) and 2,4,6-trianilino-(p-carbo-2'-ethylhexyl-1'-oxy)-1,3,5-triazine (for example Uvinul® T 150)

hexyl 2-(4-diethylamino-2-hydroxybenzoyl)benzoate (for example Uvinul® UVA Plus, BASF).

The compounds mentioned in the list should only be regarded as examples. It is of course also possible to use other UV filters. In particular, organic particulate UV filters, as described, for example, in patent application WO 99/66896, may also advantageously be combined with the nanoparticulate UV protectants according to the invention.

These organic UV filters are generally incorporated into cosmetic formulations in an amount of 0.5 to 20 percent by weight, preferably 1-10% by weight.

Further suitable organic UV filters are, for example;

2-(2H-benzotriazol-2-yl)-4-methyl-6-(2-methyl-3-(1,3,3,3-tetramethyl-1-(trimethylsilyloxy)disiloxanyl)propyl)phenol (for example Silatrizole®), 2-ethylhexyl 4,4'-[(6-[4-((1,1-dimethylethyl)aminocarbonyl)phenylamino]-1,3,5-triazine-2,4-diyl)diimino]bis (benzoate) (for example Uvasorb® HEB), α-(trimethylsilyl)-ω-[trimethylsilyl)oxy]poly[oxy(dimethyl [and approx. 6% of methyl[2-[p-[2,2-bis(ethoxycarbonyl] vinyl]phenoxy]-1-methyleneethyl] and approx. 1.5% of methyl[3-[p-[2,2-bis(ethoxycarbonyl)vinyl]phenoxy)propenyl) and 0.1 to 0.4% of (methylhydrogen]silylene]] (n≈60) (CAS No. 207 574-74-1)

2,2'-methylenebis(6-(2H-benzotriazol-2-yl)-4-(1,1,3,3-tetramethylbutyl)phenol) (CAS No. 103 597-45-1)

2,2'-(1,4-phenylene)bis(1H-benzimidazole-4,6-disulfonic acid, monosodium salt) (CAS No. 180 898-37-7) and 2,4-bis{[4-(2-ethylhexyloxy)-2-hydroxy]phenyl}-6-(4-methoxyphenyl)-1,3,5-triazine (CAS No. 103 597-45-, 187 393-00-6).

2-ethylhexyl 4,4'-[(6-[4-((1,1-dimethylethyl)aminocarbonyl)phenylamino]-1,3,5-triazine-2,4-diyl)diimino]bis (benzoate) (for example Uvasorb® HEB), Organic UV filters are generally incorporated into cosmetic formulations in a total amount of 0.5 to 20 percent by weight, preferably 1-15%.

Preferred compounds having UV-filtering properties are 3-(4'-methylbenzylidene)di-camphor, 1-(4-tert-butylphenyl)-3-(4-methoxyphenyl)propane-1,3-dione, 4-isopropyldibenzoylmethane, 2-hydroxy-4-methoxybenzophenone, octyl methoxycinnamate, 3,3,5-trimethylcyclohexyl salicylate, 2-ethylhexyl 4-(dimethylamino)benzoate, 2-ethylhexyl 2-cyano-3,3-diphenylacrylate, 2-phenylbenzimidazole-5-sulfonic acid and the potassium, sodium and triethanolamine salts thereof.

Preferred compositions may also comprise compounds of the formula I

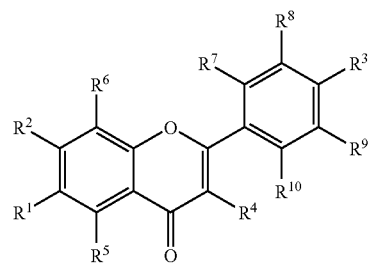

I where $R^1$ and $R^2$ are selected from
  H
  and $OR^{11}$, where $OR^{11}$, independently of one another, stands for
    OH
    straight-chain or branched $C_1$- to $C_{20}$-alkoxy groups,
    straight-chain or branched $C_3$- to $C_{20}$-alkenyloxy groups,
    straight-chain or branched $C_1$- to $C_{20}$-hydroxyalkoxy groups,
    where the hydroxyl group(s) may be bonded to a primary or secondary carbon atoms of the chain and furthermore the alkyl chain may also be interrupted by oxygen, and/or
    $C_3$- to $C_{10}$-cycloalkoxy groups and/or $C_3$- to $C_{12}$-cycloalkenyloxy groups, where the rings may each also be bridged by —$(CH_2)_n$— groups, where n=1 to 3, and/or mono- and/or oligoglycosyl radicals,
with the proviso that at least one radical from $R^1$ and $R^2$ stands for $OR^{11}$, and $R^3$ stands for a radical $OR^{11}$ and $R^4$ to $R^7$ and $R^{10}$ may be identical or different and, independently of one another, stand for

H straight-chain or branched $C_1$- to $C_{20}$-alkyl groups, straight-chain or branched $C_3$- to $C_{20}$-alkenyl groups, straight-chain or branched $C_1$- to $C_{20}$-hydroxyalkyl groups, where the hydroxyl group may be bonded to a primary or secondary carbon atom of the chain and furthermore the alkyl chain may also be interrupted by oxygen, and/or $C_3$- to $C_{10}$-cycloalkyl groups and/or $C_3$- to $C_{12}$-cycloalkenyl groups, where the rings may each also be bridged by —$(CH_2)_n$— groups, where n=1 to 3, and $R^8$ and $R^9$ may be identical or different and, independently of one another, stand for

H $OR^{11}$ straight-chain or branched $C_1$- to $C_{20}$-alkyl groups, straight-chain or branched $C_3$- to $C_{20}$-alkenyl groups, straight-chain or branched $C_1$- to $C_{20}$-hydroxyalkyl groups, where the hydroxyl group may be bonded to a primary or secondary carbon atom of the chain and furthermore the alkyl chain may also be interrupted by oxygen, and/or $C_3$- to $C_{10}$-cycloalkyl groups and/or $C_3$- to $C_{12}$-cycloalkenyl groups, where the rings may each also be bridged by —$(CH_2)_n$— groups, where n=1 to 3.

Advantages of the compositions according to the invention are, in particular, the UV light-filtering action and the good toleration by the skin. In addition, the compounds of the formula I described here are colourless or only weakly coloured and thus, in contrast to many known naturally occurring flavonoids, do not result in discoloration of the compositions.

Of the flavonoids of the formula I to be employed in accordance with the invention, broad-band UV filters [lacuna] other likewise preferred compounds of the formula I exhibit an absorption maximum in the boundary region between UV-B and UV-A radiation, As UV-A-II filters, they therefore advantageously supplement the absorption spectrum of commercially available UV-B and UV-A-I filters. Preferred compositions according to the invention having light-protection properties comprise at least one compound of the formula I, where $R^3$ stands for —OH or straight-chain or branched $C_1$- to $C_{20}$-alkoxy groups, preferably methoxy, ethoxy or ethylhexyloxy, or mono- and/or oligoglycosyl radicals, preferably glucosyl radicals, and $R^1$ and/or $R^2$ preferably stand for OH or straight-chain or branched $C_1$- to $C_{20}$-alkoxy groups, preferably methoxy, ethoxy or ethylhexyloxy, or mono- and/or oligoglycosyl radicals, preferably glucosyl radicals.

These preferred compounds are distinguished by particularly intense UV absorption.

In addition, preferred compounds of this type have advantages on incorporation into the compositions:

mono- and/or oligoglycosyl radicals improve the water solubility of the compounds to be employed in accordance with the invention;

straight-chain or branched $C_1$- to $C_{20}$-alkoxy groups, in particular the long-chain alkoxy functions, such as ethylhexyloxy groups, increase the oil solubility of the compounds;

i.e. the hydrophilicity or lipophilicity of the compounds of the formula I can be controlled via a suitable choice of the substituents. Preferred mono- or oligosaccharide radicals here are hexosyl radicals, in particular ramnosyl radicals and glucosyl radicals. However, other hexosyl radicals, for example allosyl, altrosyl, galactosyl, gulosyl, idosyl, mannosyl and talosyl, may also, if desired, advantageously be used. It may also be advantageous to use pentosyl radicals. The glycosyl radicals can be bonded to the parent structure α- or β-glycosidically. A preferred disaccharide is, for example, 6-O-(6-deoxy-α-L-mannopyranosyl)-β-D-glucopyranoside.

It has been found that the intensity of the UV absorption is particularly high if $R^3$ stands for straight-chain or branched $C_1$- to $C_{20}$-alkoxy groups, preferably methoxy, ethoxy or ethylhexyloxy, and $R^8$ and $R^9$ are identical and stand for H or straight-chain or branched $C_1$- to $C_{20}$-alkoxy groups, preferably methoxy, ethoxy or ethylhexyloxy.

Particular preference is therefore given in accordance with the invention to compositions having light-protection properties comprising at least one compound of the formula I which is characterised in that $R^3$ stands for straight-chain or branched $C_1$- to $C_{20}$-alkoxy groups, preferably methoxy, ethoxy or ethylhexyloxy, and $R^8$ and $R^9$ are identical and stand for H or straight-chain or branched $C_1$- to $C_{20}$-alkoxy groups, preferably methoxy, ethoxy or ethylhexyloxy. It is particularly preferred here if $R^8$ and $R^9$ stand for H.

The compounds of the formula I are typically employed in accordance with the invention in amounts of 0.01 to 20% by weight, preferably in amounts of 0.5% by weight to 10% by weight and particularly preferably in amounts of 1 to 8% by weight. The person skilled in the art is presented with absolutely no difficulties at all in correspondingly selecting the amounts depending on the intended light protection factor of the composition.

Combination of one or more nanoparticulate UV protectants with further UV filters enables the protective action against harmful effects of UV radiation to be optimised. Optimised compositions may comprise, for example, the combination of the organic UV filters 4'-methoxy-6-hydroxyflavone with 1-(4-tert-butylphenyl)-3-(4-methoxyphenyl) propane-1,3-dione and 3-(4'-methylbenzylidene)-dl-camphor.

All the said UV filters including the compounds of the formula I can also be employed in encapsulated form. In particular, it is advantageous to employ organic UV filters in encapsulated form. In detail, the following advantages arise:

The hydrophilicity of the capsule wall can be set independently of the solubility of the UV filter. Thus, for example, it is also possible to incorporate hydrophobic UV filters into purely aqueous compositions. In addition, the oily impression on application of the composition comprising hydrophobic UV filters, which is frequently regarded as unpleasant, is suppressed.

Certain UV filters, in particular dibenzoylmethane derivatives, exhibit only reduced photostability in cosmetic compositions. Encapsulation of these filters or compounds which impair the photostability of these filters, such as, for example, cinnamic acid derivatives, enables the photostability of the entire composition to be increased.

Skin penetration by organic UV filters and the associated potential for irritation on direct application to the human skin is repeatedly being discussed in the literature. The encapsulation of the corresponding substances which is proposed here suppresses this effect.

In general, encapsulation of individual UV filters or other ingredients enables preparation problems caused by the interaction of individual composition constituents with one another, such as crystallisation processes, precipitation and agglomeration, to be avoided since the interaction is suppressed.

It may therefore be preferred in accordance with the invention for one or more of the compounds of the formula I or the above-mentioned UV filters to be in encapsulated form. It is advantageous here for the capsules to be so small that they cannot be observed with the naked eye. In order to achieve the above-mentioned effects, it is furthermore necessary for the capsules to be sufficiently stable and the encapsulated active ingredient (UV filter) only to be released to the environment to a small extent, or not at all.

Suitable capsules can have walls of inorganic or organic polymers. For example, U.S. Pat. No. 6,242,099 B1 describes the production of suitable capsules with walls of chitin, chitin derivatives or polyhydroxylated polyamines. Capsules particularly preferably to be employed in accordance with the invention have walls which can be obtained by a sol-gel process, as described in the applications WO 00/09652, WO 00/72806 and WO 00/71084. Preference is in turn given here to capsules whose walls are built up from silica gel (silica; undefined silicon oxide hydroxide). The production of corresponding capsules is known to the person skilled in the art, for example from the cited patent applications, whose contents expressly also belong to the subject-matter of the present application.

The capsules are preferably present in compositions according to the invention in amounts which ensure that the encapsulated UV filters are present in the composition in the above-indicated amounts.

If the compositions according to the invention comprise compounds of the formula I containing free hydroxyl groups, they additionally, besides the properties described, exhibit an action as antioxidant and/or free-radical scavenger. Preference is therefore also given to compositions having light-protection properties comprising at least one compound of the formula I which is characterised in that at least one of the radicals $R^1$ to $R^3$ stands for OH, preferably with at least one of the radicals $R^1$ or $R^2$ standing for OH.

In order that the compounds of the formula I are able to develop their positive action as free-radical scavengers particularly well on the skin, it may be preferred to allow the compounds of the formula I to penetrate into deeper skin layers. Several possibilities are available for this purpose. Firstly, the compounds of the formula I can have an adequate lipophilicity in order to be able to penetrate through the outer skin layer into epidermal layers. As a further possibility, corresponding transport agents, for example liposomes, which enable transport of the compounds of the formula I through the outer skin layers may also be provided in the composition. Finally, systemic transport of the compounds of the formula I is also conceivable. The composition is then designed, for example, in such a way that it is suitable for oral administration.

In general, the substances of the formula I act as free-radical scavengers. Free radicals of this type are not generated only by sunlight, but instead are formed under various conditions. Examples are anoxia, which blocks the flow of electrons upstream of the cytochrome oxidases and causes the formation of superoxide free-radical anions; inflammation associated, inter alia, with the formation of superoxide anions by the membrane NADPH oxidase of the leucocytes, but also associated with the formation (through disproportionation in the presence of iron(II) ions) of the hydroxyl free radicals and other reactive species which are normally involved in the phenomenon of phagocytosis; and lipid autoxidation, which is generally initiated by a hydroxyl free radical and produces lipidic alkoxy free radicals and hydroperoxides.

It is assumed that preferred compounds of the formula I also act as enzyme inhibitors. They are thought to inhibit histidine decarboxylase, protein kinases, elastase, aldose reductase and hyaluronidase, and therefore enable the intactness of the basic substance of vascular sheaths to be maintained. Furthermore, they are thought to inhibit catechol O-methyl transferase non-specifically, causing the amount of available catecholamines and thus the vascular strength to be increased. Furthermore, they inhibit AMP phosphodiesterase, giving the substances potential for inhibiting thrombocyte aggregation.

Owing to these properties, the compositions according to the invention are, in general, suitable for immune protection and for the protection of DNA and RNA. In particular, the compositions are suitable for the protection of DNA and RNA against oxidative attack, against free radicals and against damage due to radiation, in particular UV radiation. A further advantage of the compositions according to the invention is cell protection, in particular protection of Langerhans cells against damage due to the above-mentioned influences. The present invention also expressly relates to all these uses and to the use of the compounds of the formula I for the preparation of compositions which can be employed correspondingly.

In particular, preferred compositions according to the invention are also suitable for the treatment of skin diseases associated with a defect in keratinisation which affects differentiation and cell proliferation, in particular for the treatment of acne vulgaris, acne comedonica, polymorphic acne, acne rosaceae, nodular acne, acne conglobata, age-induced acne, acne which arises as a side effect, such as acne solaris, medicament-induced acne or acne professionalis, for the treatment of other defects in keratinisation, in particular ichthyosis, ichthyosiform states, Darier's disease, keratosis palmoplantaris, leucoplasia, leucoplasiform states, herpes of the skin and mucous membrane (buccal) (lichen), for the treatment of other skin diseases associated with a defect in keratinisation and which have an inflammatory and/or immunoallergic component and in particular all forms of psoriasis which affect the skin, mucous membranes and fingers and toenails, and psoriatic rheumatism and skin atopy, such as eczema or respiratory atopy, or hypertrophy of the gums, it furthermore being possible for the compounds to be used for some inflammation which is not associated with a defect in keratinisation, for the treatment of all benign or malignant excrescence of the dermis or epidermis, which may be of viral origin, such as verruca vulgaris, verruca plana, epidermodysplasia verruciformis, oral papillomatosis, papillomatosis florida, and excrescence which may be caused by UV radiation, in particular epithelioma baso-cellulare and epithelioma spinocellulare, for the treatment of other skin diseases, such as dermatitis bullosa and diseases affecting the collagen, for the treatment of certain eye diseases, in particular corneal diseases, for overcoming or combating light-induced skin ageing associated with ageing, for reducing pigmentation and keratosis actinica and for the treatment of all diseases associated with normal ageing or light-induced ageing, for the prevention or healing of wounds/scars of atrophy of the epidermis and/or dermis caused by locally or systemically applied corticosteroids and all other types of skin atrophy, for the prevention or treatment of defects in wound healing, for the prevention or elimination of stretch marks caused by pregnancy or for the promotion of wound healing, for combating defects in sebum production, such as hyperseborrhoea in acne or simple seborrhoea, for combating or preventing cancer-like states or pre-carcinogenic states, in particular pro-myelocytic leukaemia, for the treatment of inflammatory diseases, such as arthritis, for the treatment of all virus-induced diseases of the skin or other areas of the body, for the prevention or treatment of alopecia, for the treatment of skin diseases or diseases of other areas of the body with an immunological component, for the treatment of cardiovascular diseases, such as arteriosclerosis or hypertension, and of non-insulin-dependent diabetes, and for the treatment of skin problems caused by UV radiation.

The protective action against oxidative stress or against the effect of free radicals can be further improved if the compositions comprise one or more antioxidants.

In a preferred embodiment of the present invention, the composition is therefore a composition for the protection of body cells against oxidative stress, in particular for reducing skin ageing, characterised in that it preferably comprises one or more antioxidants.

There are many proven substances known from the specialist literature which can be used as antioxidants, for example amino acids (for example glycine, histidine, tyrosine, tryptophan) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysteine sulfoximine, buthionine sulfones, penta-, hexa- and heptathionine sulfoximine) in very low tolerated doses (for example pmol to µmol/kg), and also (metal) chelating agents (for example α-hydroxy fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), vitamin A and derivatives (for example vitamin A palmitate), and coniferyl benzoate of benzoin resin, rutinic acid and derivatives thereof, α-glycosyl rutin, ferulic acid, furfurylideneglucitol, carnosine, butylhydroxytoluene, butylhydroxyanisole, nordihydroguaiaretic acid, trihydroxybutyrophenone, quercetin, uric acid and derivatives thereof, mannose and derivatives thereof, zinc and derivatives thereof (for example ZnO, $ZnSO_4$), selenium and derivatives thereof (for example selenomethionine), stilbenes and derivatives thereof (for example stilbene oxide, trans-stilbene oxide).

Mixtures of antioxidants are likewise suitable for use in the cosmetic compositions according to the invention. Known and commercial mixtures are, for example, mixtures comprising, as active ingredients, lecithin, L-(+)-ascorbyl palmitate and citric acid (for example Oxynex® AP), natural tocopherols, L-(+)-ascorbyl palmitate, L-(+)-ascorbic acid and citric acid (for example Oxynex® K LIQUID), tocopherol extracts from natural sources, L-(+)-ascorbyl palmitate, L-(+)-ascorbic acid and citric acid (for example Oxynex® L LIQUID), DL-α-tocopherol, L-(+)ascorbyl palmitate, citric acid and lecithin (for example Oxynex® LM) or butylhydroxytoluene (BHT), L-(+)-ascorbyl palmitate and citric acid (for example Oxynex® 2004).

The compositions according to the invention may comprise vitamins as further ingredients. The cosmetic compositions according to the invention preferably comprise vitamins and vitamin derivatives selected from vitamin A, vitamin A propionate, vitamin A palmitate, vitamin A acetate, retinol, vitamin B, thiamine chloride hydrochloride (vitamin $B_1$), riboflavin (vitamin $B_2$), nicotinamide, vitamin C (ascorbic acid), vitamin D, ergocalciferol (vitamin $D_2$), vitamin E, DL-α-tocopherol, tocopherol E acetate, tocopherol hydrogensuccinate, vitamin $K_1$, esculin (vitamin P active ingredient), thiamine (vitamin $B_1$), nicotinic acid (niacin), pyridoxine, pyridoxal, pyridoxamine (vitamin $B_6$), pantothenic acid, biotin, folic acid and cobalamine (vitamin $B_{12}$), particularly preferably vitamin A palmitate, vitamin C, DL-α-tocopherol, tocopherol E acetate, nicotinic acid, pantothenic acid and biotin.

The compositions according to the invention may in addition comprise further conventional skin-protecting or skin-care active ingredients. These can in principle be any active ingredients known to the person skilled in the art.

Particularly preferred active ingredients are pyrimidinecarboxylic acids and/or aryl oximes.

Pyrimidinecarboxylic acids occur in halophilic microorganisms and play a role in osmoregulation of these organisms (E. A. Galinski et al., *Eur. J. Biochem.*, 149 (1985) pages 135-139). Of the pyrimidinecarboxylic acids, particular mention should be made here of ectoin ((S)-1,4,5,6-tetrahydro-2-methyl-4-pyrimidinecarboxylic acid) and hydroxyectoin ((S,S)-1,4,5,6-tetrahydro-5-hydroxy-2-methyl-4-pyrimidinecarboxylic acid) and derivatives thereof. These compounds stabilise enzymes and other biomolecules in aqueous solutions and organic solvents. Furthermore, they stabilise, in particular, enzymes against denaturing conditions, such as salts, extreme pH values, surfactants, urea, guanidinium chloride and other compounds.

Ectoin and ectoin derivatives, such as hydroxyectoin, can advantageously be used in medicaments. In particular, hydroxyectoin can be employed for the preparation of a medicament for the treatment of skin diseases. Other areas of application of hydroxyectoin and other ectoin derivatives are typically in areas in which, for example, trehalose is used as additive. Thus, ectoin derivatives, such as hydroxyectoin, can be used as protectant in dried yeast and bacteria cells, Pharmaceutical products, such as non-glycosylated, pharmaceutically active peptides and proteins, for example t-PA, can also be protected with ectoin or its derivatives.

Of the cosmetic applications, particular mention should be made of the use of ectoin and ectoin derivatives for the care of aged, dry or irritated skin. Thus, European patent application EP-A-0 671 161 describes, in particular, that ectoin and hydroxyectoin are employed in cosmetic compositions, such as powders, soaps, surfactant-containing cleansing products, lipsticks, rouge, make-up, care creams and sunscreen preparations.

Preference is given here to the use of a pyrimidinecarboxylic acid of the following formula II

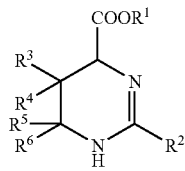

in which $R^1$ is a radical H or C1-8-alkyl, $R^2$ is a radical H or C1-4-alkyl, and $R^3$, $R^4$, $R^5$ and $R^6$ are each, independently of one another, a radical from the group consisting of H, OH, $NH_2$ and C1-4-alkyl. Preference is given to the use of pyrimidinecarboxylic acids in which $R^2$ is a methyl or ethyl group, and $R^1$ or $R^5$ and $R^6$ are H. Particular preference is given to the use of the pyrimidinecarboxylic acids ectoin ((S)-1,4,5,6-tetrahydro-2-methyl-4-pyrimidinecarboxylic acid) and hydroxyectoin ((S,S)-1,4,5,6-tetrahydro-5-hydroxy-2-methyl-4-pyrimidinecarboxylic acid). In this case, the compositions according to the invention preferably comprise pyrimidinecarboxylic acids of this type in amounts of up to 15% by weight.

Of the aryl oximes, preference is given to the use of 2-hydroxy-5-methyllaurophenone oxime, which is also known as HMLO, LPO or F5. Its suitability for use in cosmetic compositions is disclosed, for example, in DE-A-41 16 123. Compositions which comprise 2-hydroxy-5-methyllaurophenone oxime are accordingly suitable for the treatment of skin diseases which are accompanied by inflammation. It is known that compositions of this type can be used, for example, for the therapy of psoriasis, various forms of eczema, irritative and toxic dermatitis, UV dermatitis and further allergic and/or inflammatory diseases of the skin and integumentary appendages. Compositions according to the invention which comprise aryl oximes, preferably 2-hydroxy-5-methyllaurophenone oxime, exhibit surprising antiinflammatory suitability. The compositions here preferably comprise 0.01 to 10% by weight of the aryl oxime, it being particularly preferred for the composition to comprise 0.05 to 5% by weight of aryl oxime.

All compounds or components described here that can be used in the compositions are either known and commercially available or can be synthesised by known processes.

Besides the compounds described here, the compositions according to the invention may also comprise at least one photostabiliser, preferably conforming to the formula III

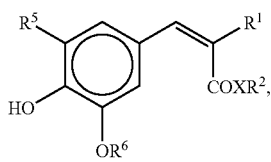

where
$R^1$ is selected from $—C(O)CH_3$, $—CO_2R^3$, $—C(O)NH_2$ and $—C(O)N(R^4)_2$;
X is O or NH;
$R^2$ stands for a linear or branched $C_{1-30}$-alkyl radical;
$R^3$ stands for a linear or branched $C_{1-20}$-alkyl radical;

all $R^4$, independently of one another, stand for H or linear or branched $C_{1-8}$-alkyl radicals;
$R^5$ stands for H, a linear or branched $C_{1-8}$-alkyl radical or a linear or branched $—O—C_{1-8}$-alkyl radical; and
$R^6$ stands for a $C_{1-8}$-alkyl radical,
where the photostabiliser is particularly preferably bis(2-ethylhexyl) 2-(4-hydroxy-3,5-dimethoxybenzylidene)malonate. Corresponding photostabilisers and their preparation and use are described in International patent application WO 03/007906, the disclosure content of which expressly also belongs to the subject-matter of the present application.

The compositions according to the invention can be prepared by processes which are well known to the person skilled in the art, in particular by the processes which serve for the preparation of oil-in-water emulsions or water-in-oil emulsions.

The present invention furthermore relates to a process for the preparation of a composition which is characterised in that at least one nanoparticulate UV protectant is mixed with a cosmetically or dermatologically suitable carrier, and to the use of nanoparticulate UV protectants for the preparation of a composition having light-protection properties.

These compositions can be, in particular, in the form of simple or complex emulsions (O/W, W/O, O/W/O or W/O/W), such as creams, milks, gels or gel creams, powders and solid sticks, and they may, if desired, be formulated as aerosols and be in the form of foams or sprays. These compositions are preferably in the form of an O/W emulsion.

The cosmetic compositions according to the invention can be used as compositions for protection of the human epidermis or of the hair against UV radiation, as sunscreen compositions or make-up products.

It should be pointed out that in the formulations according to the invention for sun protection which have a carrier of the oil-in-water emulsion type, the aqueous phase (which comprises, in particular, the hydrophilic filters) generally makes up 50 to 95% by weight and preferably 70 to 90% by weight, based on the formulation as a whole, the oil phase (which comprises, in particular, the lipophilic filters) makes up 5 to 50% by weight and preferably 10 to 30% by weight, based on the formulation as a whole, and the (co)emulsifier or (co)emulsifiers make(s) up 0.5 to 20% by weight and preferably 2 to 10% by weight, based on the formulation as a whole.

Suitable compositions are those for external use, for example in the form of a cream, lotion or gel or as a solution which can be sprayed onto the skin. Suitable for internal use are administration forms such as capsules, coated tablets, powders, tablet solutions or solutions.

Examples which may be mentioned of application forms of the compositions according to the invention are: solutions suspensions, emulsions, PIT emulsions, pastes, ointments, gels, creams, lotions, powders, soaps, surfactant-containing cleansing preparations, oils, aerosols and sprays. Examples of other application forms are sticks, shampoos and shower products. Any desired customary carriers, auxiliaries and, if desired, further active ingredients may be added to the composition.

Preferred auxiliaries originate from the group consisting of preservatives, antioxidants, stabilisers, solubilisers, vitamins, colorants and odour improvers.

Ointments, pastes, creams and gels may comprise the customary carriers, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary carriers, for example lactose, talc, silica, aluminium hydroxide, calcium silicate and polyamide powder, or mixtures of these substances. Sprays may additionally comprise the customary propellants, for example chlorofluorocarbons, propane/butane or dimethyl ether.

Solutions and emulsions may comprise the customary carriers, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, glycerol fatty acid esters, polyethylene glycols and fatty acid esters of sorbitan, or mixtures of these substances.

Suspensions may comprise the customary carriers, such as liquid diluents, for example water, ethanol or propylene glycol, suspending agents, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary carriers, such as alkali metal salts of fatty acids, salts of fatty acid monoesters, fatty acid protein hydrolysates, isethionates, lanolin, fatty alcohol, vegetable oils, plant extracts, glycerol, sugars, or mixtures of these substances.

Surfactant-containing cleansing products may comprise the customary carriers, such as salts of fatty alcohol sulfates, fatty alcohol ether sulfates, sulfosuccinic acid monoesters, fatty acid protein hydrolysates, isethionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils may comprise the customary carriers, such as synthetic oils, such as fatty acid esters, fatty alcohols, silicone oils, natural oils, such as vegetable oils and oily plant extracts, paraffin oils, lanolin oils, or mixtures of these substances.

Further typical cosmetic application forms are also lipsticks, lip-care sticks, mascara, eyeliner, eye shadow, rouge, powder make-up, emulsion make-up and wax make-up, and sunscreen, pre-sun and after-sun preparations.

The preferred composition forms according to the invention include, in particular, emulsions.

Emulsions according to the invention are advantageous and comprise, for example, the said fats, oils, waxes and other fatty substances, as well as water and an emulsifier, as usually used for a composition of this type.

The lipid phase may advantageously be selected from the following group of substances:
  mineral oils, mineral waxes
  oils, such as triglycerides of capric or caprylic acid, furthermore natural oils, such as, for example, castor oil;
  fats, waxes and other natural and synthetic fatty substances, preferably esters of fatty acids with alcohols having a low carbon number, for example with isopropanol, propylene glycol or glycerol, or esters of fatty alcohols with alkanoic acids having a low carbon number or with fatty acids;
  silicone oils, such as dimethylpolysiloxanes, diethylpolysiloxanes, diphenylpoly-siloxanes and mixed forms thereof.

For the purposes of the present invention, the oil phase of the emulsions, oleo-gels or hydrodispersions or lipodispersions is advantageously selected from the group consisting of esters of saturated and/or unsaturated, branched and/or unbranched alkanecarboxylic acids having a chain length of 3 to 30 C atoms and saturated and/or unsaturated, branched and/or unbranched alcohols having a chain length of 3 to 30 C atoms, or from the group consisting of esters of aromatic carboxylic acids and saturated and/or unsaturated, branched and/or unbranched alcohols having a chain length of 3 to 30 C atoms. Ester oils of this type can then advantageously be selected from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic semi-synthetic and natural mixtures of esters of this type, for example jojoba oil.

The oil phase may furthermore advantageously be selected from the group consisting of branched and unbranched hydrocarbons and waxes, silicone oils, dialkyl ethers, or the group consisting of saturated or unsaturated, branched or unbranched alcohols, and fatty acid triglycerides, specifically the triglycerol esters of saturated and/or unsaturated, branched and/or unbranched alkanecarboxylic acids having a chain length of 8 to 24 C atoms, in particular 12-18 C atoms. The fatty acid triglycerides may advantageously be selected, for example, from the group consisting of synthetic, semi-synthetic and natural oils, for example olive oil, sunflower oil, soya oil, peanut oil, rapeseed oil, almond oil, palm oil, coconut oil, palm kernel oil and the like.

Any desired mixtures of oil and wax components of this type may also advantageously be employed for the purposes of the present invention. It may also be advantageous to employ waxes, for example cetyl palmitate, as the only lipid component of the oil phase.

The oil phase is advantageously selected from the group consisting of 2-ethylhexyl isostearate, octyldodecanol, isotridecyl isononanoate, isoeicosane, 2-ethylhexyl cocoate, $C_{12-15}$-alkyl benzoate, caprylic/capric acid triglyceride and dicapryl ether.

Particularly advantageous are mixtures of $C_{12-15}$-alkyl benzoate and 2-ethylhexyl isostearate, mixtures of $C_{12-15}$-alkyl benzoate and isotridecyl isononanoate, as well as mixtures of $C_{12-15}$-alkyl benzoate, 2-ethylhexyl isostearate and isotridecyl isononanoate.

Of the hydrocarbons, paraffin oil, squalane and squalene may advantageously be used for the purposes of the present invention.

Furthermore, the oil phase may also advantageously have a content of cyclic or linear silicone oils or consist entirely of oils of this type, although it is preferred to use an additional content of other oil-phase components in addition to the silicone oil or the silicone oils.

The silicone oil to be used in accordance with the invention is advantageously cyclomethicone (octamethylcyclotetrasiloxane). However, it is also advantageous for the purposes of the present invention to use other silicone oils, for example hexamethylcyclotrisiloxane, polydimethylsiloxane, poly(methylphenylsiloxane).

Also particularly advantageous are mixtures of cyclomethicone and isotridecyl isononanoate and of cyclomethicone and 2-ethylhexyl isostearate.

The aqueous phase of the compositions according to the invention optionally advantageously comprises alcohols, diols or polyols having a low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols having a low carbon number, for example ethanol, isopropanol, 1,2-propanediol, glycerol, and, in particular, one or more thickeners, which may advantageously be selected from the group consisting of silicon dioxide, aluminium silicates, polysaccharides and derivatives thereof, for example hyaluronic acid, xanthan gum, hydroxypropylmethylcellulose, particularly advantageously from the group consisting of the polyacrylates, preferably a polyacrylate from the group consisting of the so-called Carbopols, for example Carbopol grades 980, 981, 1382, 2984, 5984, in each case individually or in combination.

In particular, mixtures of the above-mentioned solvents are used. In the case of alcoholic solvents, water may be a further constituent.

Emulsions according to the invention are advantageous and comprise, for example, the said fats, oils, waxes and other fatty substances, as well as water and an emulsifier, as usually used for a formulation of this type.

In a preferred embodiment, the compositions according to the invention comprise hydrophilic surfactants.

The hydrophilic surfactants are preferably selected from the group consisting of the alkylglucosides, acyl lactylates, betaines and coconut amphoacetates.

The alkylglucosides are themselves advantageously selected from the group consisting of the alkylglucosides which are distinguished by the structural formula

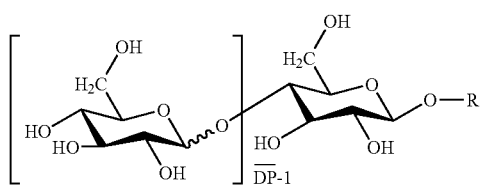

where R represents a branched or unbranched alkyl radical having from 4 to 24 carbon atoms, and where ,DP denotes a mean degree of glucosylation of up to 2.

The value ,DP represents the degree of glucosidation of the alkylglucosides used in accordance with the invention and is defined as $$\overline{DP} = \frac{p_1}{100} \cdot 1 + \frac{p_2}{100} \cdot 2 + \frac{p_3}{100} \cdot 3 + \ldots = \sum \frac{p_i}{100} \cdot i$$

in which $p_1$, $p_2$, $p_3$ ... $p_i$ represent the proportion of mono-, di-, tri- ... i-fold glucosylated products in percent by weight. Products having degrees of glucosylation of 1-2, particularly advantageously of 1.1 to 1.5, very particularly advantageously of 1.2-1.4, in particular of 1.3, are advantageously selected in accordance with the invention.

The value DP takes into account the fact that alkylglucosides are generally, as a consequence of their preparation, in the form of mixtures of mono- and oligoglucosides. A relatively high content of monoglucosides, typically in the order of 40-70% by weight, is advantageous in accordance with the invention.

Alkylglucosides which are particularly advantageously used in accordance with the invention are selected from the group consisting of octyl glucopyranoside, nonyl glucopyranoside, decyl glucopyranoside, undecyl glucopyranoside, dodecyl glucopyranoside, tetradecyl glucopyranoside and hexadecyl glucopyranoside.

It is likewise advantageous to employ natural or synthetic raw materials and auxiliaries or mixtures which are distinguished by an effective content of the active ingredients used in accordance with the invention, for example Plantaren® 1200 (Henkel KGaA), Oramix® NS 10 (Seppic).

The acyllactylates are themselves advantageously selected from the group consisting of the substances which are distinguished by the structural formula

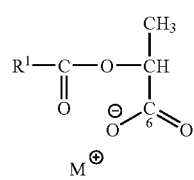

where $R^1$ denotes a branched or unbranched alkyl radical having 1 to 30 carbon atoms, and $M^+$ is selected from the group consisting of the alkali metal ions and the group consisting of ammonium ions which are substituted by one or more alkyl and/or by one or more hydroxyalkyl radicals, or corresponds to half an equivalent of an alkaline earth metal ion.

For example, sodium isostearyl lactylate, for example the product Pathionic® ISL from the American Ingredients Company, is advantageous.

The betaines are advantageously selected from the group consisting of the substances which are distinguished by the structural formula

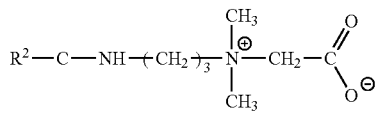

where $R^2$ denotes a branched or unbranched alkyl radical having 1 to 30 carbon atoms.

$R^2$ particularly advantageously denotes a branched or unbranched alkyl radical having 6 to 12 carbon atoms.

For example, capramidopropylbetaine, for example the product Tego® Betain 810 from Th. Goldschmidt AG, is advantageous.

A coconut amphoacetate which is advantageously selected in accordance with the invention is, for example, sodium coconut amphoacetate, as available under the name Miranol® Ultra C32 from Miranol Chemical Corp.

The compositions according to the invention are advantageously characterised in that the hydrophilic surfactant(s) is (are) present in concentrations of 0.01-20% by weight, preferably 0.05-10% by weight, particularly preferably 0.1-5% by weight, in each case based on the total weight of the composition.

For use, the cosmetic and dermatological compositions according to the invention are applied to the skin and/or the hair in an adequate amount in the usual manner for cosmetics.

Cosmetic and dermatological compositions according to the invention may exist in various forms. Thus, they may be, for example, a solution, a water-free composition, an emulsion or microemulsion of the water-in-oil (W/O) type or of the oil-in-water (O/W) type, a multiple emulsion, for example of the water-in-oil-in-water (W/O/W) type, a gel, a solid stick, an ointment or an aerosol. It is also advantageous to administer ectoins in encapsulated form, for example in collagen matrices and other conventional encapsulation materials, for example as cellulose encapsulations, in gelatine, wax matrices or liposomally encapsulated.

In particular, wax matrices, as described in DE-A 43 08 282, have proven favourable. Preference is given to emulsions. O/W emulsions are particularly preferred. Emulsions, W/O emulsions and O/W emulsions are obtainable in a conventional manner.

Emulsifiers that can be used are, for example, the known W/O and O/W emulsifiers. It is advantageous to use further conventional co-emulsifiers in the preferred O/W emulsions according to the invention.

An emulsifier that has proven to be particularly preferred in accordance with the invention for O/W emulsions is the commercial product Ceralution C from Sasol.

Co-emulsifiers which are advantageously selected in accordance with the invention are, for example, O/W emulsifiers, principally from the group consisting of the substances having HLB values of 11-16, very particularly advantageously having HLB values of 14.5-15.5, so long as the O/W emulsifiers have saturated radicals R and R'. If the O/W emulsifiers have unsaturated radicals R and/or R' or if isoalkyl derivatives are present, the preferred HLB value of such emulsifiers may also be lower or higher.

It is advantageous to select the fatty alcohol ethoxylates from the group consisting of ethoxylated stearyl alcohols, cetyl alcohols, cetylstearyl alcohols (cetearyl alcohols). Particular preference is given to the following: polyethylene glycol (13) stearyl ether (steareth-13), polyethylene glycol (14) stearyl ether (steareth-14), polyethylene glycol (15) stearyl ether (steareth-15), polyethylene glycol (16) stearyl ether (steareth-16), polyethylene glycol (17) stearyl ether (steareth-17), polyethylene glycol (18) stearyl ether (steareth-18), polyethylene glycol (19) stearyl ether (steareth-19), polyethylene glycol (20) stearyl ether (steareth-20), polyethylene glycol (12) isostearyl ether (isosteareth-12), polyethylene glycol (13) isostearyl ether (isosteareth-13), polyethylene glycol (14) isostearyl ether (isosteareth-14), polyethylene glycol (15) isostearyl ether (isosteareth-15), polyethylene glycol (16) isostearyl ether (isosteareth-16), polyethylene glycol (17) isostearyl ether (isosteareth-17), polyethylene glycol (18) isostearyl ether (isosteareth-18), polyethylene glycol (19) isostearyl ether (isosteareth-19), polyethylene glycol (20) isostearyl ether (isosteareth-20), polyethylene glycol (13) cetyl ether (ceteth-13), polyethylene glycol (14) cetyl ether (ceteth-14), polyethylene glycol (15) cetyl ether (ceteth-15), polyethylene glycol (16) cetyl ether (ceteth-16), polyethylene glycol (17) cetyl ether (ceteth-17), polyethylene glycol (18) cetyl ether (ceteth-18), polyethylene glycol (19) cetyl ether (ceteth-19), polyethylene glycol (20) cetyl ether (ceteth-20), polyethylene glycol (13) isocetyl ether (isoceteth-13), polyethylene glycol (14) isocetyl ether (isoceteth-14), polyethylene glycol (15) isocetyl ether (isoceteth-15), polyethylene glycol (16) isocetyl ether (isoceteth-16), polyethylene glycol (17) isocetyl ether (isoceteth-17), polyethylene glycol (18) isocetyl ether (isoceteth-18), polyethylene glycol (19) isocetyl ether (isoceteth-19), polyethylene glycol (20) isocetyl ether (isoceteth-20), polyethylene glycol (12) oleyl ether (oleth-12), polyethylene glycol (13) oleyl ether (oleth-13), polyethylene glycol (14) oleyl ether (oleth-14), polyethylene glycol (15) oleyl ether (oleth-15), polyethylene glycol (12) lauryl ether (laureth-12), polyethylene glycol (12) isolauryl ether (isolaureth-12), polyethylene glycol (13) cetylstearyl ether (ceteareth-13), polyethylene glycol (14) cetylstearyl ether (ceteareth-14), polyethylene glycol (15) cetylstearyl ether (ceteareth-15), polyethylene glycol (16) cetylstearyl ether (ceteareth-16), polyethylene glycol (17) cetylstearyl ether (ceteareth-17), polyethylene glycol (18) cetylstearyl ether (ceteareth-18), polyethylene glycol (19) cetylstearyl ether (ceteareth-19), polyethylene glycol (20) cetylstearyl ether (ceteareth-20).

It is furthermore advantageous to select the fatty acid ethoxylates from the following group:
polyethylene glycol (20) stearate, polyethylene glycol (21) stearate, polyethylene glycol (22) stearate, polyethylene glycol (23) stearate, polyethylene glycol (24) stearate, polyethylene glycol (25) stearate, polyethylene glycol (12) isostearate, polyethylene glycol (13) isostearate, polyethylene glycol (14) isostearate, polyethylene glycol (15) isostearate, polyethylene glycol (16) isostearate, polyethylene glycol (17) isostearate, polyethylene glycol (18) isostearate, polyethylene glycol (19) isostearate, polyethylene glycol (20) isostearate, polyethylene glycol (21) isostearate, polyethylene glycol (22) isostearate, polyethylene glycol (23) isostearate, polyethylene glycol (24) isostearate, polyethylene glycol (25) isostearate, polyethylene glycol (12) oleate, polyethylene glycol (13) oleate, polyethylene glycol (14) oleate, polyethylene glycol (15) oleate, polyethylene glycol (16) oleate, polyethylene glycol (17) oleate, polyethylene glycol (18) oleate, polyethylene glycol (19) oleate, polyethylene glycol (20) oleate.

An ethoxylated alkyl ether carboxylic acid or salt thereof which can advantageously be used is sodium laureth-11 carboxylate. An alkyl ether sulfate which can advantageously be used is sodium laureth-14 sulfate. An ethoxylated cholesterol derivative which can advantageously be used is polyethylene glycol (30) cholesteryl ether. Polyethylene glycol (25) soyasterol has also proven successful. Ethoxylated triglycerides which can advantageously be used are the polyethylene glycol (60) evening primrose glycerides.

It is furthermore advantageous to select the polyethylene glycol glycerol fatty acid esters from the group consisting of polyethylene glycol (20) glyceryl laurate, polyethylene glycol (21) glyceryl laurate, polyethylene glycol (22) glyceryl laurate, polyethylene glycol (23) glyceryl laurate, polyethylene glycol (6) glyceryl caprate/caprinate, polyethylene glycol (20) glyceryl oleate, polyethylene glycol (20) glyceryl isostearate, polyethylene glycol (18) glyceryl oleate/cocoate.

It is likewise favourable to select the sorbitan esters from the group consisting of polyethylene glycol (20) sorbitan monolaurate, polyethylene glycol (20) sorbitan monostearate, polyethylene glycol (20) sorbitan monoisostearate, polyethylene glycol (20) sorbitan monopalmitate, polyethylene glycol (20) sorbitan monooleate.

The following can be employed as optional W/O emulsifiers, but ones which may nevertheless be advantageous in accordance with the invention:
fatty alcohols having 8 to 30 carbon atoms, monoglycerol esters of saturated and/or unsaturated, branched and/or unbranched alkanecarboxylic acids having a chain length of 8 to 24, in particular 12-18 C atoms, diglycerol esters of saturated and/or unsaturated, branched and/or unbranched alkanecarboxylic acids having a chain length of 8 to 24, in particular 12-18 C atoms, monoglycerol ethers of saturated and/or unsaturated, branched and/or unbranched alcohols having a chain length of 8 to 24, in particular 12-18 C atoms, diglycerol ethers of saturated and/or unsaturated, branched and/or unbranched alcohols having a chain length of 8 to 24, in particular 12-18 C atoms, propylene glycol esters of saturated and/or unsaturated, branched and/or unbranched alkanecarboxylic acids having a chain length of 8 to 24, in particular 12-18 C atoms, and sorbitan esters of saturated and/or unsaturated, branched and/or unbranched alkanecarboxylic acids having a chain length of 8 to 24, in particular 12-18 C atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprinate, glyceryl monocaprylate.

Compositions which are preferred in accordance with the invention are particularly suitable for protecting human skin against UV-induced ageing processes and against oxidative stress, i.e. against damage caused by free radicals, as are generated, for example, by sunlight, heat or other influences. In this connection, they are in the various administration forms usually used for this application. For example, they may, in particular, be in the form of a lotion or emulsion, such as in the form of a cream or milk (O/W, W/O, O/W/O, W/O/W), in the form of oily-alcoholic, oily-aqueous or aqueous-alcoholic gels or solutions, in the form of solid sticks or may be formulated as an aerosol.

The composition may comprise cosmetic adjuvants that are usually used in this type of composition, such as, for example, thickeners, softeners, moisturisers, surface-active agents, emulsifiers, preservatives, antifoams, perfumes, waxes, lanolin, propellants, dyes and/or pigments which colour the composition itself or the skin, and other ingredients usually used in cosmetics.

The dispersant or solubiliser used can be an oil, wax or other fatty substance, a lower monoalcohol or a lower polyol or mixtures thereof. Particularly preferred monoalcohols or polyols include ethanol, i-propanol, propylene glycol, glycerol and sorbitol.

A preferred embodiment of the invention is an emulsion in the form of a protective cream or milk which, apart from the compound(s) of the formula I, comprises, for example, fatty alcohols, fatty acids, fatty acid esters, in particular triglycerides of fatty acids, lanolin, natural and synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and/or a polyol, such as glycerol, and oils, waxes and fatty acid esters, such as triglycerides of fatty acids.

The composition according to the invention may also be in the form of an alcoholic gel which comprises one or more lower alcohols or polyols, such as ethanol, propylene glycol or glycerol, and a thickener, such as siliceous earth. The oily-alcoholic gels also comprise natural or synthetic oil or wax.

The solid sticks consist of natural or synthetic waxes and oils, fatty alcohols, fatty acids, fatty acid esters, lanolin and other fatty substances.

If a composition is formulated as an aerosol, the customary propellants, such as alkanes, fluoroalkanes and chlorofluoroalkanes, are generally used.

The cosmetic composition may also be used to protect the hair against photochemical damage in order to prevent colour changes, bleaching or damage of a mechanical nature. In this case, a suitable formulation is in the form of a rinse-out shampoo, lotion, gel or emulsion, the composition in question being applied before or after shampooing, before or after colouring or bleaching or before or after permanent waving. It is also possible to select a composition in the form of a lotion or gel for styling and treating the hair, in the form of a lotion or gel for brushing or laying a water wave, in the form of a hair lacquer, permanent-waving composition, colorant or bleach for the hair. The composition having light-protection properties may comprise various adjuvants used in this type of composition, such as surface-active agents, thickeners, polymers, softeners, preservatives, foam stabilisers, electrolytes, organic solvents, silicone derivatives, oils, waxes, antigrease agents, dyes and/or pigments which colour the composition itself or the hair, or other ingredients usually used for hair care.

The invention is explained in greater detail below with reference to examples.

EXAMPLES

Example 1a

Preparation of Nano-$TiO_2$ 710 ml of sodium titanate (content 140 g of $TiO_2$/l), obtained by reaction of meta-titanic acid with sodium hydroxide solution, is diluted with 100 ml of water and decomposed by addition of hydrochloric acid at pH 2.2-2.6 with formation of titanium dioxide (rutile). This nanoparticulate titanium dioxide obtained by the decomposition is peptised with addition of 115 ml of 30% hydrochloric acid and made up to a total volume of 1000 ml by further addition of water. The peptisation is carried out in a sealed glass flask at 105° C. over a period of 2 h. The product exhibits needle-shaped crystallites (FIG. 1)

Example 1b

Preparation of Nano-$TiO_2$

After peptisation is complete, the experiment product obtained from experiment 1a is subjected to further hydrothermal treatment in a pressure container at a temperature of 180° C. for a period of 2 h. The resultant product exhibits oval crystallites (FIG. 2)

Example 2a

Coating of the Nano-$TiO_2$ with $SiO_2$ 1 l of the aqueous hydrochloric acid suspension of $TiO_2$ from Example 1b is brought to a pH of 6.5 using NaOH and heated to 80° C. 52 ml of water-glass solution (corresponding to 384 g of $SiO_2$/l) are subsequently added to the suspension at constant pH (pH=6.5±0.5; regulation by addition of $H_2SO_4$). When the addition is complete, the mixture is stirred at pH=6.8 and 80° C. for 2 hours. The product is subsequently washed to a conductivity of less than 100 µS/cm and dried.

Example 2b

Coating of the Nano-$TiO_2$ with $SiO_2$ 1 l of the aqueous hydrochloric acid suspension of $TiO_2$ from Example 1b is brought to a pH of 9.0 using NaOH and heated to 80° C. 52 ml of water-glass solution (corresponding to 384 g of $SiO_2$/l) are subsequently added to the suspension at constant pH (pH=9.0±0.5, regulation by addition of $H_2SO_4$). When the addition is complete, the mixture is stirred at pH=6.8 and 80° C. for 2 hours. The product is subsequently washed to a conductivity of less than 100 µS/cm and dried.

Example 2c

Coating of the Nano-TiO$_2$ with SiO$_2$ 1 l of the aqueous hydrochloric acid suspension of TiO$_2$ from Example 1b is brought to a pH of 2.0 using NaOH and heated to 80° C. 52 ml of water-glass solution (corresponding to 384 g of SiO$_2$/l) are subsequently added to the suspension at constant pH (pH=2.0±0.5; regulation by addition of H$_2$SO$_4$). When the addition is complete, the mixture is stirred at pH=6.8 and 80° C. for 2 hours. The product is subsequently washed to a conductivity of less than 100 µS/cm and dried.

Example 2d

Coating of the Nano-TiO$_2$ with SiO$_2$ 1 l of the aqueous hydrochloric acid suspension of TiO$_2$ from Example 1b is brought to a pH of 9.0 using NaOH and heated to 80° C. 52 ml of water-glass solution (corresponding to 384 g of SiO$_2$/l) are subsequently added to the suspension. During this addition, the pH rises to about 10.6. When the addition is complete, the pH is lowered to 6.5 by addition of sulfuric acid, and the mixture is then stirred at pH=6.8 and 80° C. for 2 hours. The product is subsequently washed to a conductivity of less than 100 µS/cm and dried.

Example 3

Preparation of a Light-Protection Composition Comprising TiO$_2$ and 4,4'-Methoxy-Tert-Butyldibenzoylmethane Formulations corresponding to Formulation Example 6 (see further below) are prepared using the following titanium dioxide grades Example 3a: titanium dioxide according to the invention as in Example 2a Example 3b: titanium dioxide with aluminium-containing coating (commercial product MT 100 Z; Tayca)

The content of 4,4'-methoxy-tert-butyldibenzoylmethane in the formulations is determined by means of HPLC as a measure of the storage stability of this compound after storage of the formulations under various conditions.

Sample Preparation:

About 0.1 g of the homogenised formulation are weighed out to analytical accuracy in a 100 ml volumetric flask and dispersed with about 10 ml of water, subsequently made up to the measurement mark with methanol.

Factor Sample Weight:

Weigh out about 30 mg of 4,4'-methoxy-tert-butyldibenzoylmethane, weighed to analytical accuracy, in a 100 ml volumetric flask and make up to the measurement mark with methanol. Make up 10.0 ml of this solution to the measurement mark with methanol in a 100 ml volumetric flask. Equals the factor solution.

Chromatographic Conditions:

| | |
|---|---|
| Column: | Superspher 100 RP18e; 125-4, Cat. 1.16855 |
| Column temperature: | 25° C. |
| Eluent: | methanol/mixture A (20:80 v/v) 1.5 ml/min. Mixture A: mixture on 1 l of ammonium acetate solution = 0.005 mol/l and 2 ml of acetic acid 100% |
| Gradient: | isocratic |
| Detection: | variable UV detector; 320 nm |
| Metering: | 10 µl metering loop |
| Instrument: | for example Hewlett-Packard System 1100 liquid chromatograph |
| Evaluation: | area evaluation by the external standard method. |

Measurements were carried out at the following times:

A: immediately after preparation of the formulation
B: after storage for 4 weeks at room temperature in the dark
C: after storage for 4 weeks at 5° C. in the dark
D: after storage for 4 weeks at 40° C. in the dark
E: after storage for 12 weeks at room temperature in the dark
F: after storage for 12 weeks at 5° C. in the dark
G: after storage for 12 weeks at 40° C. in the dark The results are shown in FIG. 3. It can be seen that the content of 4,4'-methoxy-tert-butyldibenzoylmethane in Comparative Example 3b has already dropped after storage for 4 weeks at elevated temperature in the dark, while no degradation is evident in the example according to the invention. Even after storage for 12 weeks, the content of 4,4'-methoxy-tert-butyldibenzoylmethane changes only little in the example according to the invention, while substantial degradation is observed in the comparative example (40° C. in the dark).

The same results are obtained with the products from Examples 2b, 2c and 2d.

Example 4

Discoloration Test in Cosmetic Formulations with UV Irradiation

Formulations are prepared as described in Formulation Example 6. In each case one comprises the titanium dioxide according to the invention from Examples 2a-d, while a commercially available titanium dioxide with trimethoxyoctylsilane coating (Uvinul™ TiO$_2$; BASF) is employed in the comparative sample.

3 g of each of the formulations are placed in a PMMA Petri dish and irradiated for 58 minutes in the sun test (Suntest CPS with xenon lamp; solar standard filter+cover sheet for sample protection (limiting of the radiation to ≥290 nm); Radialux with UV sensor) at a maximum irradiation strength of 87 W/m$^2$ (UV region)=2 MED skin type II (corresponds to 500 J/m$^2$).

The samples are assessed visually before and after the irradiation:

| | Before | After 2 MED |
|---|---|---|
| With titanium dioxide acc. to Example 2a: | white | white |
| With titanium dioxide acc. to Example 2b: | white | white |
| With titanium dioxide acc. to Example 2c: | white | white |
| With titanium dioxide acc. to Example 2d: | white | white |
| With comparative substance: | white | yellowish |

Example 5

Crystal Formation in Cosmetic Composition

The titanium dioxides mentioned in the table are incorporated into the formulation described in accordance with the recipe described below and investigated microscopically immediately after preparation and after storage for 12 weeks at room temperature. The formulations are stable for 3 months on storage at RT/5° C./40° C. and in the rocking test at −5° C./40° C.

| Titanium dioxide type | Microscopy after preparation | Microscopy after storage for 12 weeks at room temperature in the dark |
|---|---|---|
| Titanium dioxide (according to the invention as per Example 2a) | no crystals | no crystals |
| Titanium dioxide (aluminium-containing coating) | no crystals | readily visible crystals - length about 10-100 μm |

Microscope used: Zeiss, Axioskop 2; manual version with microscope camera and PC coupling, objectives 10× Ph1, 40× Ph2, 100× pH3; polarising filter (λ4 leaves)

The same results as with Example 2a are obtained with the products from Example 2b, 2c and 2d.

Formulation:

| Raw material (INCI) | % |
|---|---|
| A | |
| Titanium dioxide (Example 2a) | 4.00 |
| Octyl methoxycinnamate | 6.00 |
| Butyl methoxydibenzoylmethane | 1.00 |
| PEG-30 dipolyhydroxystearate | 2.00 |
| PEG-30 dipolyhydroxystearate | 4.00 |
| C 12-15 alkyl benzoate | 6.00 |
| Isohexadecan | 6.00 |
| Cyclomethicone | 2.00 |
| Microcrystalline wax | 2.00 |
| PVP/Eicosene copolymer | 1.00 |
| Tocopheryl acetate | 1.00 |
| B | |
| Glycerin | 3.00 |
| Sodium chloride | 0.40 |
| Propylene glycol (and) diazolidinyl urea and) methylparaben (and) propylparaben | 0.50 |
| Water | 67.10 |

Preparation:

Combine phase A apart from titanium dioxide and heat to 80° C. Stir titanium dioxide slowly into the hot oil phase and homogenise for 30 seconds with the hand mixer at setting 4. Heat phase B to 80° C. and slowly add to phase A with stirring, homogenise for 1 minute at about 60° C. with the hand mixer at setting 4 and cool and deaerate with stirring.

Example 6

Discoloration of Cosmetic Formulations During Storage

Formulations corresponding to Formulation Example 6 are prepared with the following titanium dioxide grades Example 6a: titanium dioxide according to the invention as per Example 2a Example 6b: titanium dioxide with aluminium-containing coating (commercial product MT 100 Z; Tayca)

Example 6c: commercially available titanium dioxide (commercial product T-805; Degussa)

The formulations are stored for 3 months at 50° C. in the dark. The samples are subsequently measured in a plastic sample holder with quartz cover in a CE7000 colorimeter (Gretag-Macbeth) using a barium sulfate-lined Ulbricht sphere (measurement optics: diffuse; 8°; illuminant C, standard observer, no gloss). The measurement is evaluated in accordance with the L*a*b* system (CIELab, DIN 6174). The measurement values are shown in the following table and in FIG. 4.

| Sample | b* value |
|---|---|
| 6a | 3.52 |
| 6b | 5.35 |
| 6c | 10.59 |

The discoloration of sample 6a comprising the titanium dioxide according to the invention is significantly less after storage for 3 months than the discoloration of the two samples comprising commercially available titanium dioxide grades.

Formulation Example 1

Sunscreen Soft Cream (O/W)

SPF 6 (Sun Protection Factor, Colipa Method with 5 Test Subjects)

| Raw material (INCI) | % by wt. |
|---|---|
| A | |
| Product from Example 2a | 3.00 |
| Steareth-10, Steareth-7, Stearyl alcohol | 2.00 |
| Glyceryl stearate, Ceteth-20 | 2.00 |
| Glyceryl stearate | 3.00 |
| Microwax | 1.00 |
| Oleyl oleate | 6.00 |
| Cetearyl octanoate | 14.00 |
| Caprylic/capric triglyceride | 4.00 |
| Propylparaben | 0.05 |
| B | |
| Propylene glycol | 4.00 |
| Allantoin | 0.20 |
| Water | 60.60 |
| Methylparaben | 0.15 |

Preparation:

Heat phase A and phase B to 80° C. Slowly add phase B to phase A with stirring, homogenise and cool with stirring.

Formulation Example 2

Sunscreen Spray Lotion (O/W)

SPF 18 (Sun Protection Factor, AMA Laboratories, Inc., USA, with 5 Test Subjects)

| Raw material (INCI) | % |
|---|---|
| A | |
| Ethylhexyl methoxycinnamate, BHT | 5.00 |
| Product from Example 2b | 4.00 |
| Glyceryl stearate, cetyl alcohol, PEG-75 stearate, ceteth-20, stearth-20 | 3.30 |
| PPG-1-PEG-9 lauryl glycol ether | 0.50 |
| Diisostearoyl trimethylolpropane Siloxy silicate | 1.50 |
| $C_{12-15}$ alkyl benzoate | 3.00 |
| Dioctyl adipate | 4.00 |
| Dimethicone | 2.00 |

-continued

| Raw material (INCI) | % |
|---|---|
| B | |
| Dimethicone copolyol phosphate | 2.50 |
| Butylene glycol | 2.50 |
| Water | 70.50 |
| C | |
| PPG-1 Trideceth-6, polyquaternium-37, propylene glycol dicaprylate/dicaprate | 0.47 |
| D | |
| Propylene glycol, DMMDM hydantoin, methylparaben, propylparaben | 0.73 |

Preparation:

Combine phase A apart from the titanium dioxide and heat to 60° C. incorporate titanium dioxide slowly into the molten oil phase. Heat phase B to 60° C., then disperse phase C in with stirring. Stir phase A into phase B/C with high input of energy. Cool with stirring, and add phase D at 40° C. Homogenise and cool to 25° C. with stirring.

Formulation Example 3

Sunscreen Soft Cream (O/W)

SPF 23 (Sun Protection Factor, Colipa Method with 5 Test Subjects)

| Raw material (INCI) | % |
|---|---|
| A | |
| Product from Example 2c | 10.00 |
| Steareth-10, steareth-7, stearyl alcohol | 3.00 |
| Glyceryl stearate, ceteth-20 | 3.00 |
| Glyceryl stearate | 3.00 |
| Microwax | 1.00 |
| Oleyl oleate | 4.00 |
| Cetearyl octanoate | 10.50 |
| Caprylic/capric triglyceride | 4.00 |
| Propylparaben | 0.05 |
| B | |
| Propylene glycol | 4.00 |
| Allantoin | 0.20 |
| Water | 57.10 |
| Methylparaben | 0.15 |

Preparation:

Heat phase A and B to 80° C. Slowly add phase B to phase A with stirring, homogenise and cool with stirring.

Formulation Example 4

Sunscreen Lotion (O/W)

| Raw material (INCI) | % |
|---|---|
| A | |
| Ethylhexyl methoxycinnamate, BHT | 6.00 |
| Butyl methoxydibenzoylmethane | 1.00 |
| Polyglyceryl-3 methylglucose distearate | 4.00 |
| Ethylhexyl stearate | 8.00 |
| Cetearyl isononanoate | 2.00 |

-continued

| Raw material (INCI) | % |
|---|---|
| PVP/eicosene copolymer | 1.00 |
| Tocopheryl acetate | 1.00 |
| B | |
| Xanthan gum | 0.30 |
| Sodium cetearyl sulfate | 1.00 |
| Glycerin | 5.00 |
| Water | 65.70 |
| C | |
| Product from Example 2a | 4.00 |
| D | |
| Phenoxyethanol, butylparaben, ethylparaben, propylparaben, methylparaben | 1.00 |

Preparation:

Heat phase A to 80° C. Pre-swell the Keltrol of phase B in the water, then add the remaining raw materials and heat to 80° C. Add phase A to phase B and homogenise for 2 min. (rod mixer): cool with stirring and add phase C at 35° C., Homogenise again for 1 min. (rod mixer). Cool to room temperature and stir in phase D.

Formulation Example 5

Sunscreen Lotion (O/W)

In Vivo SPF 17±3 (Colipa Method with 10 Test Subjects)

| Raw material (INCI) | % |
|---|---|
| A | |
| Product from Example 2d | 5.00 |
| Ethylhexyl methoxycinnamate, BHT | 5.00 |
| Glyceryl stearate, cetyl alcohol, PEG-75 stearate, ceteth-20, steareth-20 | 3.30 |
| PPG-1-PEG-9 lauryl glycol ether | 0.50 |
| Diisostearoyl trimethylolpropane siloxy silicate | 1.50 |
| C12-15 Alkyl benzoate | 3.00 |
| Dioctyl adipate | 4.00 |
| Dimethicone | 2.00 |
| B | |
| Ectoin | 0.10 |
| Allantoin | 0.20 |
| Dimethicone copolyol phosphate | 2.50 |
| Butylene glycol | 2.50 |
| Water | 68.90 |
| C | |
| PPG-1 trideceth-6, polyquaternium-37, propylene glycol dicaprylate/dicaprate | 0.47 |
| D | |
| Propylene glycol, DMMDM hydantoin, ethylparaben | 0.73 |
| Perfume | 0.30 |

Preparation:

Combine phase A apart from the titanium dioxide and heat to 60° C. Slowly incorporate titanium dioxide into the molten oil phase. Heat phase B to 60° C., then disperse phase C in with stirring. Stir phase A into phase B/C with vigorous stirring. Cool with stirring and add phase D at 40° C. Homogenise and cool to 25° C. with stirring.

Formulation Example 6

Sunscreen Lotion (O/W)

| Raw material (INCI) | % |
|---|---|
| A | |
| Product from Example 3a or 3b | 5.00 |
| Butylmethoxy dibenzoylmethane | 3.00 |
| Steareth-10, steareth-7, stearyl alcohol | 3.00 |
| Glyceryl stearate, ceteth-20 | 3.00 |
| Glyceryl stearate | 3.00 |
| Microwax | 1.00 |
| Oleyl oleate | 4.43 |
| Cetearyl octanoate | 11.64 |
| Caprylic/capric triglyceride | 4.43 |
| Propylparaben | 0.05 |
| B | |
| Propylene glycol | 4.00 |
| Allantoin | 0.20 |
| Water | 57.10 |
| Methylparaben | 0.15 |

Preparation:

Heat phase A and B to 80° C. Slowly add phase B to phase A with stirring, homogenise and cool with stirring.

Formulation Example 7

Sunscreen Lotion (O/W)

SPF 10 (Sun Protection Factor, Colipa Method with 10 Test Subjects)

| A | |
|---|---|
| Steareth-10, steareth-7, stearyl alcohol | 3.00 |
| Glyceryl stearate, ceteth-20 | 3.00 |
| Cetearyl octanoate | 15.50 |
| Glyceryl stearate | 3.00 |
| Oleyl oleate | 7.00 |
| Microwax | 1.00 |
| Caprylic/capric triglyceride | 6.00 |
| Propylparaben | 0.05 |
| B | |
| 33% aqueous dispersion of the product from Example 2a | 16.70 |
| Propylene glycol | 4.00 |
| Allantoin | 0.20 |
| Water | 40.40 |
| Methylparaben | 0.15 |

Preparation:

Heat phase A to 75° C. and phase B to 80° C. Slowly stir phase B into phase A, Homogenise and cool with stirring.

Formulation Example 8

Sunscreen Spray Lotion (O/W)

SPF 31 (Sun Protection Factor, FDA Method with 5 Test Subjects at AMA Laboratories)

| A | |
|---|---|
| Product from Example 2d | 5.00 |
| Ethylhexyl methoxycinnamate, BHT | 7.50 |
| Benzophenone-3 | 2.50 |
| PEG-100 stearate, glyceryl stearate | 2.80 |
| PPG-1-PEG-9 lauryl glycol ether | 0.40 |
| Dicapryl ether | 4.50 |
| Steareth-10 | 0.50 |
| Stearyl alcohol | 0.60 |
| Dimethicone | 2.00 |
| B | |
| Dimethicone copolyol phosphate | 2.50 |
| Chitosan glycolate | 2.00 |
| Glycerin | 2.50 |
| Water | 66.10 |
| C | |
| PPG-1 trideceth-6, polyquaternium-37, propylene glycol dicaprylate/dicaprate | 0.40 |
| D | |
| Propylene glycol, DMMDM hydantoin, methylparaben, propylparaben | 0.70 |

Preparation:

Combine phase A apart from the titanium dioxide and heat to 60° C. Slowly incorporate titanium dioxide into the molten oil phase. Heat phase B-1 to 60° C., then disperse phase B-2 in with stirring. Stir phase A into phase B with high input of energy. Cool with stirring, and add phase C at 40° C. Homogenise and cool to 25° C. with stirring.

Formulation Example 9

Sunscreen Cream, High SPF, Water-Resistant (O/W)

With Eusolex® UV-Pearls™ OMC, SPF (In Vitro, Diffey Method) 64±12, UVA-PF 17

| A | |
|---|---|
| Water | 38.30 |
| Glycerin | 3.00 |
| Pentylene glycol | 3.00 |
| PVP/hexadedecene copolymer | 1.00 |
| Sodium cetearyl sulfate | 1.00 |
| Xanthan gum | 0.20 |
| B | |
| Glyceryl stearate, cetearyl alcohol, sodium stearoyl lactylate, tocopherol | 5.00 |
| Tri-C12-13 alkyl citrate | 3.50 |
| Isopropylphthalimide, butylphthalide | 5.00 |
| Caprylic/capric triglyceride | 2.50 |
| C12-15 alkyl benzoate | 2.00 |
| Cyclomethicone | 0.80 |
| Tocopheryl acetate | 1.00 |
| Butylmethoxydibenzoylmethane | 1.00 |
| Benzophenone-3 | 2.00 |
| Product from Example 2a | 4.00 |
| C | |
| Water, ethylhexyl methoxycinnamate, silica, PVP, chlorphenesin, BHT (Eusolex UV Pearl OMC) | 20.00 |

-continued

| | |
|---|---|
| D | |
| Carbomer | 0.15 |
| Water | 4.85 |
| E | |
| Sodium hydroxide | 0.90 |
| F | |
| Phenoxyethanol, butylparaben, ethylparaben, propylparaben, methylparaben | 0.50 |
| Perfume | 0.30 |

Preparation:

Heat phases A and B to 80° C. separately from one another. Homogenise phase B using the Thurrax until the pigment is well wetted. Add phase B to phase A and homogenise for 2 min. Cool to 35° C., add phase C and homogenise for 30 sec. Add phase D and homogenise for 30 sec. Stir in phase E and neutralise using phase F and homogenise until satisfactory pigment distribution has been achieved (microscopic check!). Cool to room temperature, deaerate and stir in phase G.

Formulation Example 10

Sun Protection Lotion (PEG-Free)

In Vitro SPF (Diffey) 12±2

| Raw material (INCI) | % |
|---|---|
| A | |
| C12-15 Alkyl benzoate | 3.00 |
| Decyl cocoate | 4.00 |
| Ethylhexyl palmitate | 3.00 |
| Glyceryl stearate | 0.50 |
| Stearic acid | 0.50 |
| Tocopheryl acetate | 0.50 |
| B | |
| Cetearyl glucoside | 1.50 |
| Propylene glycol | 2.00 |
| Glycerin | 1.00 |
| Water | 76.80 |
| C | |
| Product from Example 2a | 5.00 |
| D | |
| Carbomer | 0.20 |
| Paraffinum liquidum (mineral oil) | 0.80 |
| E | |
| Sodium hydroxide | 0.50 |
| F | |
| Propylene glycol, diazolidinylurea, methylparaben, propylparaben | 0.50 |
| Perfume | 0.20 |

Preparation:

Heat phase A and phase B separately to 80° C. Add phase A to phase B with stirring. Incorporate phase C into the emulsion at 40° C. with stirring and homogenise until the pigment distribution is optimal. Add phase D at 35° C. and again homogenise briefly. Add phase E, check the pH and again homogenise briefly. Add phase F and stir until cold.

Formulation Example 11

W/O Sunscreen Lotion

With Inorganic Filter, In Vitro SPF (Diffey Method) 8.7±1.6, UVA-PF 4.4±0.5

| Raw material (INCI) | % |
|---|---|
| A | |
| Cetyl PEG/PPG-10/1 Dimethicone | 2.50 |
| Stearoxy dimethicone | 0.25 |
| Ethylhexyl stearate | 12.75 |
| Ethylhexyl palmitate | 8.00 |
| Isohexadecane | 7.00 |
| hydrogenate castor oil | 0.50 |
| Ceresin (microcrystalline wax) | 1.00 |
| B | |
| Product from Example 2b | 5.00 |
| C | |
| Water | 62.00 |
| Sodium chloride | 0.50 |
| Propylene glycol, diazolidinyl urea, methylparaben, propylparaben | 0.50 |

Preparation:

Heat phase A to 80° C. Carefully incorporate the titanium dioxide (phase B) into the hot oil phase. Slowly add phase C to phase A/B with stirring (500 rpm, (Mig stirrer). Homogenise for 2 minutes at 1600 rpm. Cool to about 40° C. with stirring about 300 rpm) and again homogenise for 2 minutes at 1600 rpm.

Formulation Example 12

Illustrative formulations for cosmetic compositions which are obtained in the same way with titanium dioxide from Example 2a, 2b, 2c or 2d (in each case referred to as titanium dioxide in the table) are indicated below. In addition, the INCI names of the commercially available compounds are indicated.

UV-Pearl, OMC stands for the composition with the INCI name:

Water (for EU: Aqua), Ethylhexyl Methoxycinnamate, Silica, PVP, Chlorphenesin, BHT; this composition is commercially available under the name Eusolex® UV Pearl™ OMC from Merck KGaA, Darmstadt.

The other UV-Pearl indicated in the tables each have an analogous composition with OMC replaced by the UV filters indicated.

TABLE 1

| W/O emulsions (numbers in % by weight) | | | | | | | | | | |
|---|---|---|---|---|---|---|---|---|---|---|
| | 1-1 | 1-2 | 1-3 | 1-4 | 1-5 | 1-6 | 1-7 | 1-8 | 1-9 | 1-10 |
| Titanium dioxide | 3 | 2 | 5 | 10 | 7 | 4 | 15 | 1 | 3 | 3 |
| Butylmethoxydibenzoyl-methane | 5 | 3 | 2 | 1 | 2 | | | | 1 | 1 |
| Zinc oxide | | | | | | | | 5 | 2 | |

TABLE 1-continued

W/O emulsions (numbers in % by weight)

| | | | | | | | | | | |
|---|---|---|---|---|---|---|---|---|---|---|
| UV-Pearl, OMC | 30 | 15 | 15 | 15 | 15 | 15 | 15 | 15 | 15 | 15 |
| Polyglyceryl-3-Dimerate | 3 | 3 | 3 | 3 | 3 | 3 | 3 | 3 | 3 | 3 |
| Cera Alba | 0.3 | 0.3 | 0.3 | 0.3 | 0.3 | 0.3 | 0.3 | 0.3 | 0.3 | 0.3 |
| Hydrogenated Castor Oil | 0.2 | 0.2 | 0.2 | 0.2 | 0.2 | 0.2 | 0.2 | 0.2 | 0.2 | 0.2 |
| Paraffinium Liquidum | 7 | 7 | 7 | 7 | 7 | 7 | 7 | 7 | 7 | 7 |
| Caprylic/Capric Triglyceride | 7 | 7 | 7 | 7 | 7 | 7 | 7 | 7 | 7 | 7 |
| Hexyl Laurate | 4 | 4 | 4 | 4 | 4 | 4 | 4 | 4 | 4 | 4 |
| PVP/Eicosene Copolymer | 2 | 2 | 2 | 2 | 2 | 2 | 2 | 2 | 2 | 2 |
| Propylene Glycol | 4 | 4 | 4 | 4 | 4 | 4 | 4 | 4 | 4 | 4 |
| Magnesium Sulfate | 0.6 | 0.6 | 0.6 | 0.6 | 0.6 | 0.6 | 0.6 | 0.6 | 0.6 | 0.6 |
| Tocopherol | 0.5 | 0.5 | 0.5 | 0.5 | 0.5 | 0.5 | 0.5 | 0.5 | 0.5 | 0.5 |
| Tocopheryl Acetate | 0.5 | 0.5 | 0.5 | 0.5 | 0.5 | 0.5 | 0.5 | 0.5 | 0.5 | 0.5 |
| Cyclomethicone | 0.5 | 0.5 | 0.5 | 0.5 | 0.5 | 0.5 | 0.5 | 0.5 | 0.5 | 0.5 |
| Propylparaben | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 |
| Water | to 100 | to 100 | to 100 | to 100 | to 100 | to 100 | to 100 | to 100 | to 100 | to 100 |

| | 1-11 | 1-12 | 1-13 | 1-14 | 1-15 | 1-16 | 1-17 | 1-18 |
|---|---|---|---|---|---|---|---|---|
| Titanium dioxide | 3 | 5 | 2 | 4 | 3 | 1 | 2 | 5 |
| Benzylidene malonate polysiloxane | | 1 | 0.5 | | | | | |
| Methylene Bis-Benztriazolyl Tetramethylbutylphenol | 1 | 1 | 0.5 | | | | | |
| Dihydroxyavcetone | 5 | 3 | 2 | 5 | 1 | 3 | 7 | 2 |
| Polyglyceryl-3-Dimerate | 3 | 3 | 3 | 3 | | | | |
| Cera Alba | 0.3 | 0.3 | 0.3 | 0.3 | 2 | 2 | 2 | 2 |
| Hydrogenated Castor Oil | 0.2 | 0.2 | 0.2 | 0.2 | | | | |
| Paraffinium Liquidum | 7 | 7 | 7 | 7 | | | | |
| Caprylic/Capric Triglyceride | 7 | 7 | 7 | 7 | | | | |
| Hexyl Laurate | 4 | 4 | 4 | 4 | | | | |
| PVP/Eicosene Copolymer | 2 | 2 | 2 | 2 | | | | |
| Propylene Glycol | 4 | 4 | 4 | 4 | | | | |
| Magnesium Sulfate | 0.6 | 0.6 | 0.6 | 0.6 | | | | |
| Tocopherol | 0.5 | 0.5 | 0.5 | 0.5 | | | | |
| Tocopheryl Acetate | 0.5 | 0.5 | 0.5 | 0.5 | 1 | 1 | 1 | 1 |
| Cyclomethicone | 0.5 | 0.5 | 0.5 | 0.5 | | | | |
| Propylparaben | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 |
| Dicocoyl Pentyerythrityl Citrate (and) Sorbitan Sesquioleate (and) Cera Alba (and) Aluminium Stearate | | | | | 6 | 6 | 6 | 6 |
| PEG-7 Hydrogenated Castor Oil | | | | | 1 | 1 | 1 | 1 |
| Zinc Stearate | | | | | 2 | 2 | 2 | 2 |
| Oleyl Erucate | | | | | 6 | 6 | 6 | 6 |
| Decyl Oleate | | | | | 6 | 6 | 6 | 6 |
| Dimethicone | | | | | 5 | 5 | 5 | 5 |
| Trometamine | | | | | 1 | 1 | 1 | 1 |
| Glycerin | | | | | 5 | 5 | 5 | 5 |
| Allantoin | | | | | 0.2 | 0.2 | 0.2 | 0.2 |
| Water | to 100 | to 100 | to 100 | to 100 | to 100 | to 100 | to 100 | to 100 |

| | 1-19 | 1-20 | 1-21 | 1-22 | 1-23 | 1-24 | 1-25 | 1-26 | 1-27 | 1-28 | 1-29 |
|---|---|---|---|---|---|---|---|---|---|---|---|
| Titanium dioxide | 1 | 2 | 5 | 1 | 3 | 4 | 5 | 2 | 3 | 3 | 3 |
| Benzylidene malonate polysiloxane | | | | 1 | | | | | 1 | 1 | |
| Methylene Bis-Benztriazolyl Tetramethylbutylphenol | | | | | | 1 | 2 | 1 | | | 1 |
| Zinc oxide | | | | | | | | | 5 | 2 | |
| UV-Pearl OMC | 5 | 5 | 5 | 5 | 7 | 5 | 5 | 5 | 5 | 5 | 8 |
| UV-Pearl, OCR | | 10 | | | | | | | | | 5 |
| UV-Pearl, EthylhexylDimethylPABA | | | 10 | | | | | | | | |
| UV-Pearl, Homosalate | | | | 10 | | | | | | | |
| UV-Pearl, Ethylhexyl salicylate | | | | | 10 | | | | | | |
| UV-Pearl, OMC, BP-3 | | | | | | 10 | | | | | |
| UV-Pearl, OCR, BP-3 | | | | | | | 10 | | | | |
| UV-Pearl, Ethylhexyl Dimethyl PABA, BP-3 | | | | | | | | 10 | | | |
| UV-Pearl, Homosalate, BP-3 | | | | | | | | | 10 | | |
| UV-Pearl, Ethylhexyl salicylate, BP-3 | | | | | | | | | | 10 | |
| Butylmethoxydibenzoylmethane | | | | | | | | | | | 2 |

TABLE 1-continued

W/O emulsions (numbers in % by weight)

| | | | | | | | | | | | |
|---|---|---|---|---|---|---|---|---|---|---|---|
| UV-Pearl OMC, 4-Methyl-benzylidene Camphor | 25 | | | | | | | | | | |
| Polyglyceryl-3-Dimerate | 3 | 3 | 3 | 3 | 3 | 3 | 3 | 3 | 3 | 3 | 3 |
| Cera Alba | 0.3 | 0.3 | 0.3 | 0.3 | 0.3 | 0.3 | 0.3 | 0.3 | 0.3 | 0.3 | 0.3 |
| Hydrogenated Castor Oil | 0.2 | 0.2 | 0.2 | 0.2 | 0.2 | 0.2 | 0.2 | 0.2 | 0.2 | 0.2 | 0.2 |
| Paraffinium Liquidum | 7 | 7 | 7 | 7 | 7 | 7 | 7 | 7 | 7 | 7 | 7 |
| Caprylic/Capric Triglyceride | 7 | 7 | 7 | 7 | 7 | 7 | 7 | 7 | 7 | 7 | 7 |
| Hexyl Laurate | 4 | 4 | 4 | 4 | 4 | 4 | 4 | 4 | 4 | 4 | 4 |
| PVP/Eicosene Copolymer | 2 | 2 | 2 | 2 | 2 | 2 | 2 | 2 | 2 | 2 | 2 |
| Propylene Glycol | 4 | 4 | 4 | 4 | 4 | 4 | 4 | 4 | 4 | 4 | 4 |
| Magnesium Sulfate | 0.6 | 0.6 | 0.6 | 0.6 | 0.6 | 0.6 | 0.6 | 0.6 | 0.6 | 0.6 | 0.6 |
| Tocopherol | 0.5 | 0.5 | 0.5 | 0.5 | 0.5 | 0.5 | 0.5 | 0.5 | 0.5 | 0.5 | 0.5 |
| Tocopheryl Acetate | 0.5 | 0.5 | 0.5 | 0.5 | 0.5 | 0.5 | 0.5 | 0.5 | 0.5 | 0.5 | 0.5 |
| Cyclomethicone | 0.5 | 0.5 | 0.5 | 0.5 | 0.5 | 0.5 | 0.5 | 0.5 | 0.5 | 0.5 | 0.5 |
| Propylparaben | 0.05 | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 | 0.15 |
| Water | | | | | | to 100 | | | | | |

TABLE 2

O/W emulsions, numbers in % by weight

| | 2-1 | 2-2 | 2-3 | 2-4 | 2-5 | 2-6 | 2-7 | 2-8 | 2-9 | 2-10 |
|---|---|---|---|---|---|---|---|---|---|---|
| Titanium dioxide | 3 | 2 | 5 | 2 | 5 | 2 | 5 | 2 | 5 | 3 |
| Methylene Bis-Benztriazolyl Tetramethylbutylphenol | | | | | | 1 | 2 | 1 | | |
| Butylmethoxydibenzoyl-methane | 3 | 3 | 3 | 3 | 3 | 3 | 3 | 3 | 3 | 3 |
| Bis(2-ethyl-hexyl) 2-(4-Hydroxy-3,5-dimethoxy-benzylidene)malonate | 1 | 5 | 4 | | 6 | | 7 | | 2 | 1 |
| 4-Methylbenzylidene Camphor | 2 | | 3 | | 4 | | 3 | | 2 | |
| Stearyl Alcohol (and) Steareth-7 (and) Steareth-10 | 3 | 3 | 3 | 3 | 3 | 3 | 3 | 3 | 3 | 3 |
| Glyceryl Stearate (and) Ceteth-20 | 3 | 3 | 3 | 3 | 3 | 3 | 3 | 3 | 3 | 3 |
| Microwax | 1 | 1 | 1 | 1 | 1 | 1 | 1 | 1 | 1 | 1 |
| Cetearyl Octanoate | 11.5 | 11.5 | 11.5 | 11.5 | 11.5 | 11.5 | 11.5 | 11.5 | 11.5 | 11.5 |
| Caprylic/Capric Triglyceride | 6 | 6 | 6 | 6 | 6 | 6 | 6 | 6 | 6 | 6 |
| Oleyl Oleate | 6 | 6 | 6 | 6 | 6 | 6 | 6 | 6 | 6 | 6 |
| Propylene Glycol | 4 | 4 | 4 | 4 | 4 | 4 | 4 | 4 | 4 | 4 |
| Propylparaben | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 |
| Trometamine | | | 1.8 | | | | | | | |
| Water | to 100 | to 100 | to 100 | to 100 | to 100 | to 100 | to 100 | to 100 | to 100 | to 100 |

| | 2-11 | 2-12 | 2-13 | 2-14 | 2-15 | 2-16 | 2-17 | 2-18 |
|---|---|---|---|---|---|---|---|---|
| Titanium dioxide | 3 | 1 | 2 | 5 | 4 | 3 | 2 | 5 |
| Benzylidene malonate polysiloxane | | 1 | 0.5 | | | | | |
| Methylene Bis-Benztriazolyl Tetramethylbutylphenol | 1 | 1 | 0.5 | | | | | |
| Butylmethoxydibenzoylmethane | 3 | 3 | 3 | 3 | 3 | 3 | 3 | 3 |
| Bis(2-ethyl-hexyl) 2-(4-Hydroxy-3,5-dimethoxy-benzylidene)malonate | 1 | 5 | 4 | | 6 | | 7 | |
| Zinc oxide | | | | 2 | | | | |
| UV-Pearl, OMC | 15 | 15 | 15 | 30 | 30 | 30 | 15 | 15 |
| 4-Methylbenzylidene Camphor | | | | 3 | | | | |
| Phenylbenzimidazole Sulfonic Acid | | | | | 4 | | | |
| Stearyl Alcohol (and) Steareth-7 (and) Steareth-10 | 3 | 3 | 3 | 3 | | | | |
| Glyceryl Stearate | 3 | 3 | 3 | 3 | | | | |
| Microwax | 1 | 1 | 1 | 1 | | | | |
| Cetearyl Octanoate | 11.5 | 11.5 | 11.5 | 11.5 | | | | |
| Caprylic/Capric Triglyceride | 6 | 6 | 6 | 6 | 14 | 14 | 14 | 14 |
| Oleyl Oleate | 6 | 6 | 6 | 6 | | | | |
| Propylene Glycol | 4 | 4 | 4 | 4 | | | | |
| Glyceryl Stearate SE | | | | | 6 | 6 | 6 | 6 |
| Stearic Acid | | | | | 2 | 2 | 2 | 2 |

TABLE 2-continued

O/W emulsions, numbers in % by weight

| | | | | | | | | |
|---|---|---|---|---|---|---|---|---|
| Persea Gratissima | | | | | 8 | 8 | 8 | 8 |
| Propylparaben | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 |
| Tromethamine | | | | 1.8 | | | | |
| Glycerin | | | | | 3 | 3 | 3 | 3 |
| Water | to 100 | to 100 | to 100 | to 100 | to 100 | to 100 | to 100 | to 100 |

| | 2-19 | 2-20 | 2-21 | 2-22 | 2-23 | 2-24 | 2-25 | 2-26 | 2-27 | 2-28 |
|---|---|---|---|---|---|---|---|---|---|---|
| Titanium dioxide | 10 | 5 | 7 | 8 | 2 | 1 | 3 | 3 | 6 | 2 |
| Benzylidene malonate polysiloxane | 1 | 2 | | | 1 | 1 | | | 1 | 0.5 |
| Butylmethoxydibenzoyl-methane | 3 | 3 | 3 | 3 | 3 | 3 | 3 | 3 | 3 | 3 |
| Octocrylene | 1 | 5 | 4 | | 6 | | 7 | | 2 | 1 |
| Methylene Bis-Benztriazolyl Tetramethylbutylphenol | | 1 | 2 | 1 | | | | 1 | 1 | 0.5 |
| Zinc oxide | | | | | 5 | 2 | | | | 2 |
| UV-Pearl, OMC | 15 | 15 | 15 | 15 | 15 | 15 | 15 | 15 | 15 | 15 |
| Caprylic/Capric Triglyceride | 14 | 14 | 14 | 14 | 14 | 14 | 14 | 14 | 14 | 14 |
| Glyceryl Stearate SE | 6 | 6 | 6 | 6 | 6 | 6 | 6 | 6 | 6 | 6 |
| Stearic Acid | 2 | 2 | 2 | 2 | 2 | 2 | 2 | 2 | 2 | 2 |
| Persea Gratissima | 8 | 8 | 8 | 8 | 8 | 8 | 8 | 8 | 8 | 8 |
| Propylparaben | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 |
| Glycerin | 3 | 3 | 3 | 3 | 3 | 3 | 3 | 3 | 3 | 3 |
| Water | to 100 | to 100 | to 100 | to 100 | to 100 | to 100 | to 100 | to 100 | to 100 | to 100 |

TABLE 3

Gels, numbers in % by weight

| | 3-1 | 3-2 | 3-3 | 3-4 | 3-5 | 3-6 | 3-7 | 3-8 | 3-9 | 3-10 |
|---|---|---|---|---|---|---|---|---|---|---|
| a = aqueaous gel | | | | | | | | | | |
| Titanium dioxide | 5 | 2 | 5 | 1 | 1 | 1 | 1 | 1 | 3 | 3 |
| Butylmethoxydibenzoylmethane | 2 | 2 | 2 | 2 | 2 | 2 | 2 | 2 | 2 | 2 |
| Dihydroxyacetone | 1 | 5 | 4 | | 6 | | 7 | | 2 | 1 |
| Benzylidene malonate polysiloxane | | | | 1 | 1 | 2 | | | 1 | 1 |
| Methylene Bis-Benztriazolyl Tetramethylbutylphenol | | 1 | | | | 1 | 2 | 1 | | |
| Zinc oxide | | | | | 2 | | | | 5 | 2 |
| UV-Pearl, Ethylhexyl Methoxycinnamate | 30 | 15 | 15 | 15 | 15 | 15 | 15 | 15 | 15 | 15 |
| 4-Methylbenzylidene Camphor | | | | | 2 | | | | | |
| Prunus Dulcis | 5 | 5 | 5 | 5 | 5 | 5 | 5 | 5 | 5 | 5 |
| Tocopheryl Acetate | 0.5 | 0.5 | 0.5 | 0.5 | 0.5 | 0.5 | 0.5 | 0.5 | 0.5 | 0.5 |
| Caprylic/Capric Triglyceride | 3 | 3 | 3 | 3 | 3 | 3 | 3 | 3 | 3 | 3 |
| Octyldodecanol | 2 | 2 | 2 | 2 | 2 | 2 | 2 | 2 | 2 | 2 |
| Decyl Oleate | 2 | 2 | 2 | 2 | 2 | 2 | 2 | 2 | 2 | 2 |
| PEG-8 (and) Tocopherol (and) Ascorbyl Palmitate (and) Ascorbic Acid (and) Citric Acid | 0.05 | 0.05 | 0.05 | 0.05 | 0.05 | 0.05 | 0.05 | 0.05 | 0.05 | 0.05 |
| Sorbitol | 4 | 4 | 4 | 4 | 4 | 4 | 4 | 4 | 4 | 4 |
| Polyacrylamide (and) C13-14 Isoparaffin (and) Laureth-7 | 3 | 3 | 3 | 3 | 3 | 3 | 3 | 3 | 3 | 3 |
| Propylparaben | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 |
| Tromethamine | | | 1.8 | | | | | | | |
| Water | to 100 | to 100 | to 100 | to 100 | to 100 | to 100 | to 100 | to 100 | to 100 | to 100 |

| | 3-11 | 3-12 | 3-13 |
|---|---|---|---|
| a = aqueaous gel | | | |
| Titanium dioxide | 3 | 1 | 2 |
| Benzylidene malonate polysiloxane | | 1 | 0.5 |
| Methylene Bis-Benztriazolyl Tetramethylbutylphenol | 1 | 1 | 0.5 |
| Butylmethoxydibenzoylmethane | 2 | 2 | 2 |

TABLE 3-continued

| Gels, numbers in % by weight | | | |
|---|---|---|---|
| Bis-(2-ethyl-hexyl) 2-(4-Hydroxy-3,5-dimethoxy-benzylidene)-malonate | 1 | 5 | 4 |
| Zinc oxide | | | 2 |
| UV-Pearl, Ethylhexyl Methoxycinnamate | 15 | 15 | 15 |
| *Prunus Dulcis* | 5 | 5 | 5 |
| Tocopheryl Acetate | 0.5 | 0.5 | 0.5 |
| Caprylic/Capric Triglyceride | 3 | 3 | 3 |
| Octyldodecanol | 2 | 2 | 2 |
| Decyl Oleate | 2 | 2 | 2 |
| PEG-8 (and) Tocopherol (and) Ascorbyl Palmitate (and) Ascorbic Acid (and) Citric Acid | 0.05 | 0.05 | 0.05 |
| Sorbitol | 4 | 4 | 4 |
| Polyacrylamide (and) C13-14 Isoparaffin (and) Laureth-7 | 3 | 3 | 3 |
| Carbomer | | | |
| Propylparaben | 0.05 | 0.05 | 0.05 |
| Methylparaben | 0.15 | 0.15 | 0.15 |
| Allantoin | | | |
| Tromethamine | | | |
| Water | to 100 | to 100 | to 100 |

| | 3-14 | 3-15 | 3-16 | 3-17 | 3-18 | 3-19 | 3-20 | 3-21 |
|---|---|---|---|---|---|---|---|---|
| Titanium dioxide | 1 | 5 | 3 | 1 | 2 | 8 | 12 | 1 |
| Butylmethoxydibenzoylmethane | 2 | 2 | 2 | 2 | 2 | 2 | 2 | 2 |
| UV-Pearl, OMC | 15 | 10 | | 10 | 10 | 10 | 15 | 10 |
| UV-Pearl, OCR | | | 10 | | | | | |
| UV-Pearl, OMC, Methylene Bis-Benztriazolyl Tetramethylbutylphenol | | 7 | | 6 | | | | |
| UV-Pearl, Ethylhexyl salicylate, Butylmethoxydibenzoylmethane | | | 10 | | | | | |
| Disodium Phenyl Dibenzimidazole Tetrasulfonate | | 3 | | | | 3 | | 3 |
| Phenylbenzimidazole Sulfonic Acid | | 2 | | | 2 | 3 | | 3 |
| *Prunus Dulcis* | 5 | 5 | 5 | | | | | |
| Tocopheryl Acetate | 0.5 | 0.5 | 0.5 | | | | | |
| Caprylic/Capric Triglyceride | 3 | 3 | 3 | | | | | |
| Octyldodecanol | 2 | 2 | 2 | | | | | |
| Decyl Oleate | 2 | 2 | 2 | | | | | |
| PEG-8 (and) Tocopherol (and) Ascorbyl Palmitate (and) Ascorbic Acid (and) Citric Acid | 0.05 | 0.05 | 0.05 | | | | | |
| Sorbitol | 4 | 4 | 4 | 5 | 5 | 5 | 5 | 5 |
| Polyacrylamide (and) C13-14 Isoparaffin (and) Laureth-7 | 3 | 3 | 3 | | | | | |
| Carbomer | | | | 1.5 | 1.5 | 1.5 | 1.5 | 1.5 |
| Propylparaben | 0.05 | 0.05 | 0.05 | | | | | |
| Methylparaben | 0.15 | 0.15 | 0.15 | 0.15 | 0.15 | 0.15 | 0.15 | 0.15 |
| Allantoin | | | | 0.2 | 0.2 | 0.2 | 0.2 | 0.2 |
| Tromethamine | | | | 2.4 | 2.4 | 2.4 | 2.4 | 2.4 |
| Water | to 100 | to 100 | to 100 | to 100 | to 100 | to 100 | to 100 | to 100 |

Formulation Example 13

Sunscreen Spray

| | | |
|---|---|---|
| A) | CERALUTION ® C; Sasol | 15.0% |
| B) | Product according to Example 2a | 5.0% |
| | Ethylhexyl Methoxycinnamate | 4.8% |
| | Ethylhexyl Salicylate | 4.8% |
| | Tocopheryl Acetate | 0.6% |
| | Cyclomethicone | 1.0% |
| | C12-15 Alkyl Benzoate | 2.5% |
| | Tridecyl Salicylate | 2.5% |
| C) | Water (Aqua), Deionised | 38.3% |
| | Water (Aqua), Deionised with 4% Avicel CL 611 (Microcrystalline Cellulose (and) Cellulose Gum) | 25.0% |
| D) | Phenoxyethanol (and) Methylparaben (and) Ethylparaben (and) Butylparaben (and) Propylparaben (and) Isobutylparaben) | 0.5% |
| E) | Fragrance | q.s. |

Preparation: phase B is slowly added to phase A at room temperature with stirring. Phase C is then added. Phases D and E are subsequently added.

INCI Ceralution® C:

Aqua (and) Capric/Caprylic triglyceride (and) Glycerin (and) Ceteareth-25 (and) Sodium Dicocoylethylenediamine PEG-15 Sulfate (and) Sodium Lauroyl Lactylate (and) Behenyl Alcohol (and) Glyceryl Stearate (and) Glyceryl Stearate Citrate (and) Gum Arabic (and) Xanthan Gum (and) Phenoxyethanol (and) Methylparaben (and) Ethylparaben (and) Butylparaben (and) Isobutylparaben Formulation Example 14

Sunscreen Lotion (O/W); SPF 7.6 (Sun Protection Factor, Diffey Method)

|  | % |
|---|---|
| A | |
| Stearyl Alcohol (and) Steareth-7 (and) Steareth-10 | 3.00 |
| Glyceryl Stearate (and) Ceteth-20 | 3.00 |
| Cetearyl Octanoate | 15.50 |
| Glyceryl Stearate | 3.00 |
| Oleyl Oleate | 7.00 |
| Microwax | 1.00 |
| Caprylic/Capric Triglyceride | 6.00 |
| B | |
| Product from Example 2c | 5.00 |
| Propylene Glycol | 4.00 |
| Preservative | q.s. |
| Water, demineralised | to 100.00 |

Preparation:

Stir titanium dioxide into phase B and heat to 80° C. Heat phase A to 75° C. Slowly add phase B to phase A with stirring, homogenise and cool with stirring.

Formulation Example 15

Sun Cream without Organ. Filters (W/O); In Vitro SPF (Diffey) 32+/−5

| Raw material | INCI | [%] |
|---|---|---|
| A | | |
| Water, demineralised | AQUA (WATER) | 53.40 |
| Polyethylene glycol 400 | PEG-8 | 4.00 |
| Pemulen TR-1 | ACRYLATES/C10-30 ALKYL ACRYLATE CROSSPOLYMER | 0.20 |
| Sodium hydroxide solution, 10% | SODIUM HYDROXIDE | 0.90 |
| STEPAN-MILD RM-1 | SODIUM STEARYL PHTHALAMATE | 1.00 |
| B1 | | |
| Ceraphyl 368 | ETHYLHEXYL PALMITATE | 10.00 |
| Zinc oxide | ZINC OXIDE | 3.00 |
| Imwitor 900 | GLYCERYL STEARATE | 0.50 |
| Jojoba oil | BUXUS CHINENSIS (JOJOBA OIL) | 1.00 |
| B2 | | |
| Germaben II | PROPYLENE GLYCOL, DIAZOLIDINYL, UREA, METHYLPARABEN, PROPYLPARABEN | 1.00 |
| Tegosoft TN | C12-15 ALKYL BENZOATE | 15.00 |
| Antaron V-216 | PVP/HEXADECENE COPOLYMER | 2.00 |
| Product from Example 2d | | 8.00 |

Preparation:
1. Introduce water into vessel with heating means and stirrer (for example Eurostar digital mixer, IKA).
2. Add PEG-400, then introduce Pemulen TR-1 into the water phase with stirring until it is homogeneously distributed.
3. Add sodium hydroxide solution in order to activate the Pemulen TR-1, stir until a clear gel is formed.
4. Heat the water phase to 72-75° C.
5. Introduce Stepan-Mild RM1 at 70° C. at a low stirrer speed and heat to 70-72° C. Stir at this temperature for at least 15 minutes until the Stepanmild RM1 is well distributed.
6. Prepare oil phase in a separate vessel and heat to 75° C. Add Imwitor 900 and jojoba oil at 60° C. Continue heating and add oil phase B to the water phase at 75° C. at an increased stirrer speed and continue stirring for 10 minutes.
7, Prepare oil phase B2 in a further vessel. Heat Tegosoft TN and Antaron V-216 to 85° C. Add titanium dioxide at 75° C. and disperse for 20 minutes until good pigment distribution has been achieved, homogenise if necessary. Add oil phase B2 to the emulsion from point 6 and continue emulsifying at 72-75° C. for 20-25 minutes.
9. Start cooling with moderate stirrer power.
10. Add Germaben II at <40° C. with stirring.
11. Homogenise in the U-Turax for 5 minutes at 5000 rpm at t<35° C.
13. Cool to room temperature and deaerate
14. Leave to rest overnight and package next day

DESCRIPTION OF THE FIGURES

FIG. 1: Transmission electron photomicrograph of titanium dioxide crystallites produced as described in Example 1a.

FIG. 2: Transmission electron photomicrograph of titanium dioxide crystallites produced as described in Example 2a.

Measurement Points
A: immediately after preparation of the formulation
B: storage for 4 weeks at room temperature in the dark
C: storage for 4 weeks at 5° C. in the dark
D: storage for 4 weeks at 40° C. in the dark
E: storage for 12 weeks at room temperature in the dark F: storage for 12 weeks at 50° C. in the dark G: storage for 12 weeks at 40° C. in the dark

Figure 1:
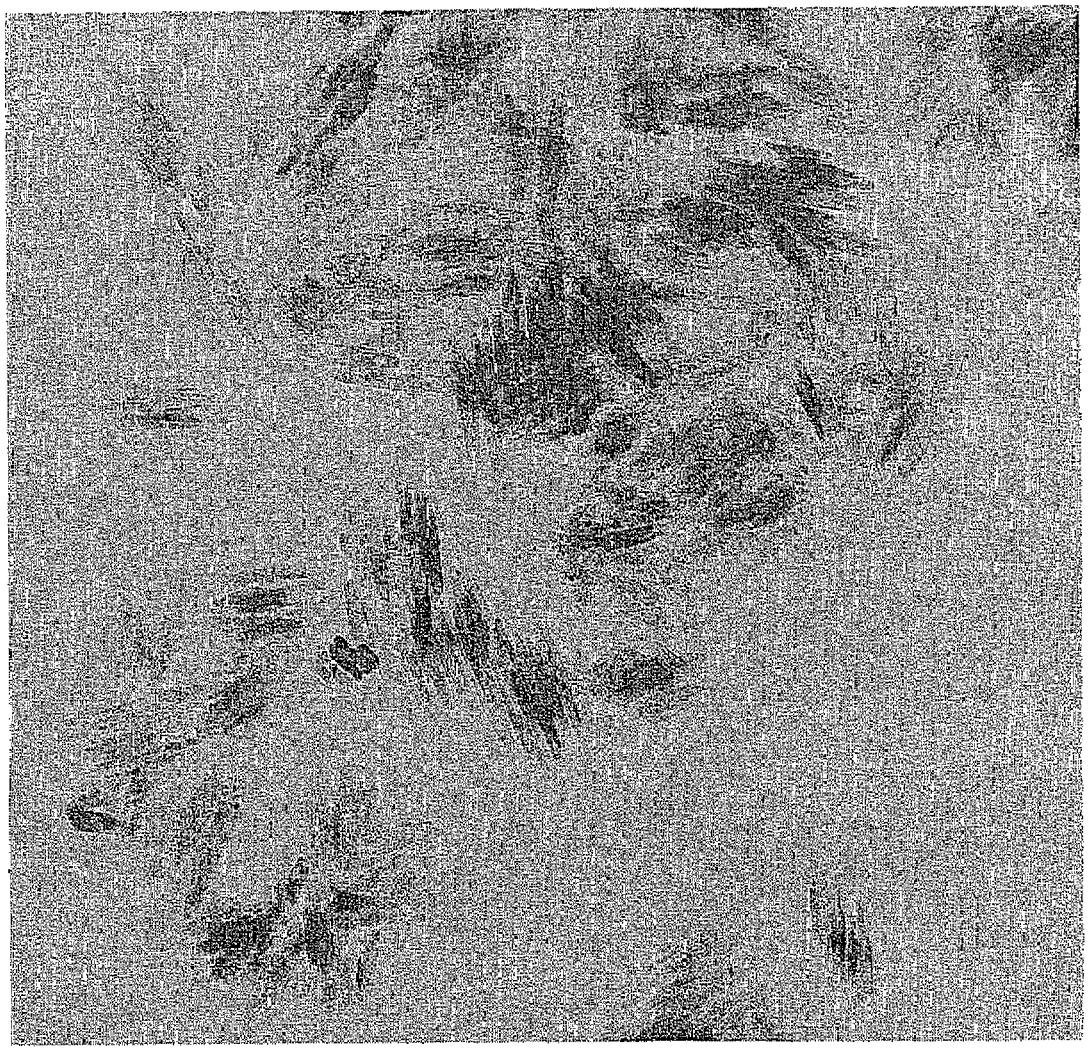
Figure 2:
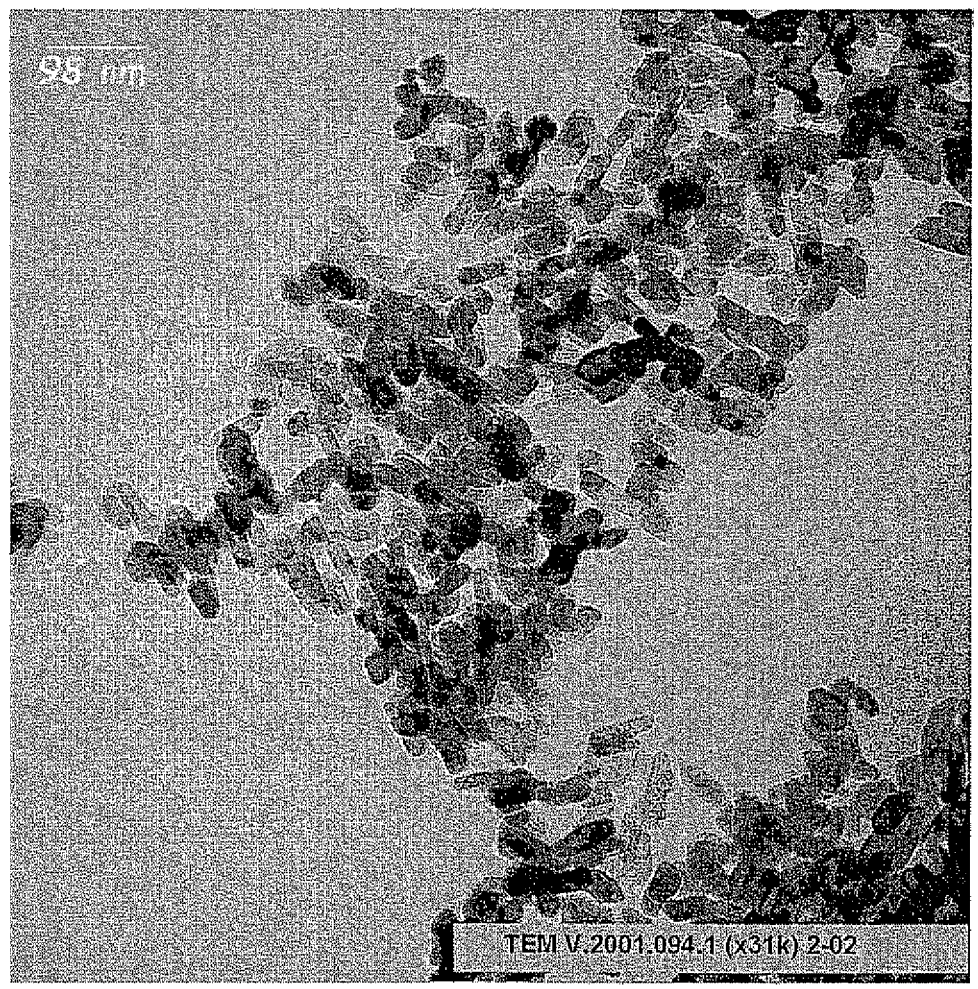
Figure 3:
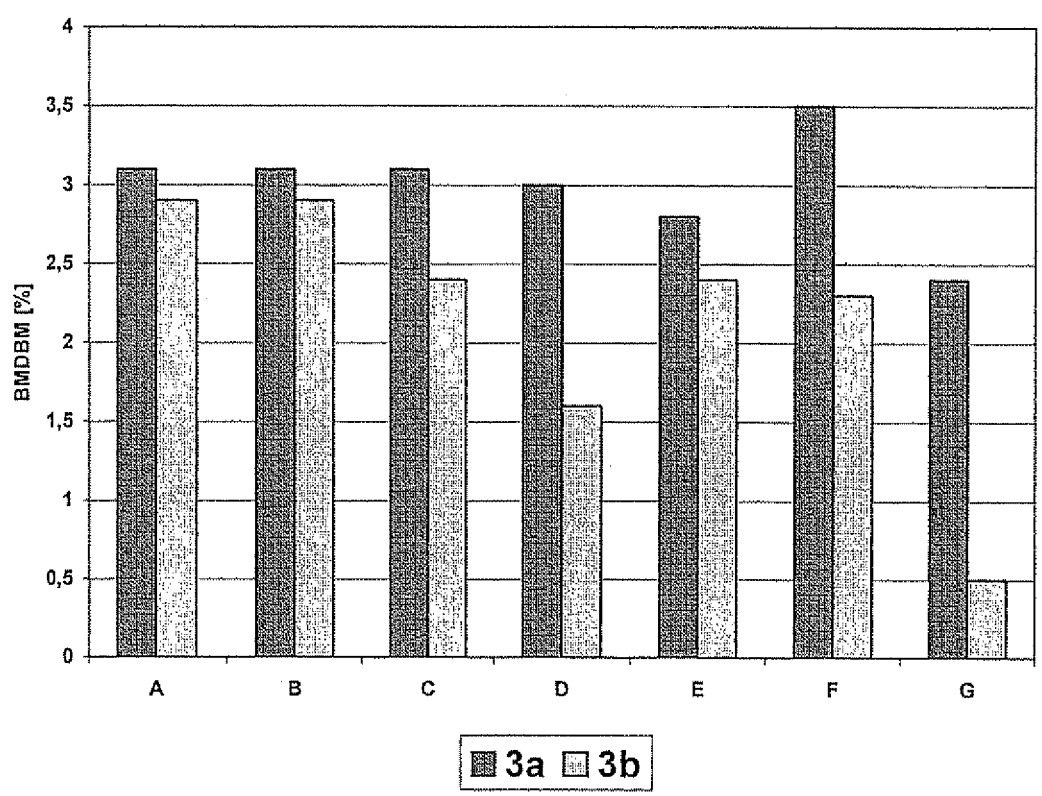
FIG. 3: Content of 4,4'-methoxy-tert-butyldibenzoylmethane (BMDBM) in formulations with titanium dioxide as a function of the storage conditions as described in Example 3; initial concentration 3% of BMDBM; (Example 3a: example according to the invention; Example 3b: comparative example)
Figure 4:
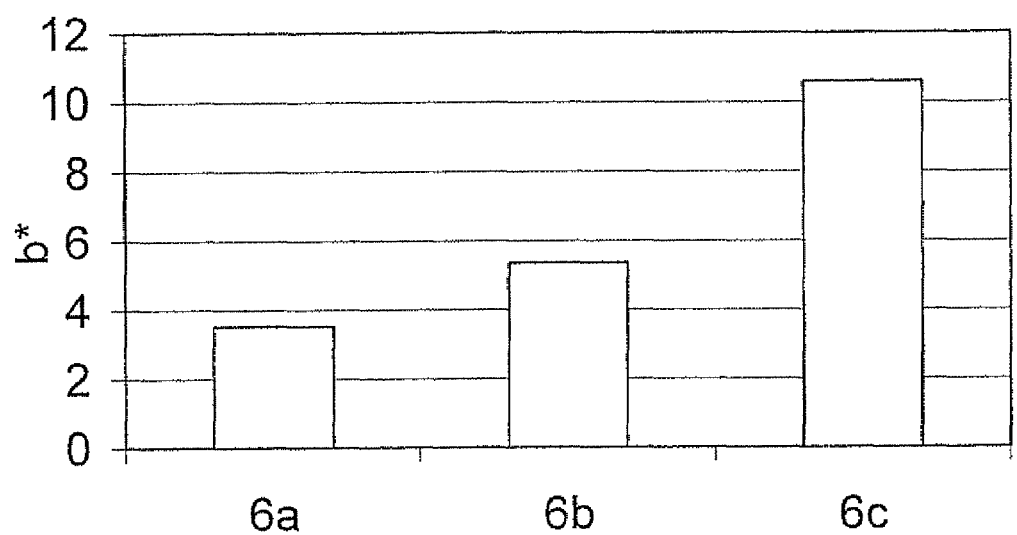
FIG. 4: b* values (L*a*b* system; CIELab, DIN 6174) of cosmetic formulations after storage for 3 months at 60° C. in the dark as described in Example 6.

The invention claimed is:

1. A process for preparing a nanoparticulate UV protectant, comprising
   a) subjecting a nanoparticulate titanium dioxide to hydrothermal treatment,
      wherein the titanium dioxide has been prepared by a process that includes peptising said titanium dioxide, and
      wherein the hydrothermal treatment is carried out in a closed container at a temperature of 140° C. to 220° C.,
   and
   b) subsequently applying a silicon dioxide coating onto said nanoparticulate titanium dioxide by a sol-gel process,
   in which a water-glass solution is added to a suspension of the titanium dioxide, wherein
      the application of the silicon dioxide coating is carried out at a pH kept constant in the range of pH=2 to pH=11, or
      the application of the silicon dioxide coating is carried out without pH regulation after prior pH adjustment of the suspension of the titanium dioxide to a value of pH=7 to pH=11, and the pH is subsequently lowered to a pH=5 to pH=8,
   and wherein the resultant coating is matured for 1 h to 8 h at a temperature of 50° C. to 110° C.

2. A process according to claim 1, wherein the hydrothermal treatment is carried out at a temperature of 140° C. to 200° C.

3. A process according to claim 1, wherein the hydrothermal treatment is carried out at a temperature of 140° C. to 180° C.

4. A process according to claim 1, wherein the hydrothermal treatment is carried out at a temperature of 150° C. to 180° C.

5. A process according to claim 1, wherein b) is carried out at a pH kept constant in the range of pH=2 to pH=11.

6. A process according to claim 1, wherein b) is carried out without pH regulation after prior pH adjustment of the suspension of the titanium dioxide to a value of pH=7 to pH=11, and the pH is subsequently lowered to a pH=5 to pH=8.

7. A process according to claim 1, wherein step b) is carried out at a temperature of 50° C. to 100° C.

8. A process according to claim 1, wherein the nanoparticulate titanium dioxide in the nanoparticulate UV protectant have a crystallite size of 5 nm to 100 nm, determined by the Scherrer method, and the dimensions of the nanoparticulate titanium dioxide, which can be determined in a transmission electron microscope, are at a length of 5 to 150 nm and a width of 5 to 60 nm.

9. A process according to claim 1, wherein the silicon dioxide coating is, based on the nanoparticulate UV protectant, 5 to 50% by weight.

10. A process according to claim 1, wherein the nanoparticulate UV protectant has a particle size determined by the Scherrer method of 5 nm to 100 nm, and the dimensions of the nanoparticulate UV protectant, which can be determined in a transmission electron microscope, are at a length of 5 to 160 nm and a width of 10 to 70 nm.

11. A process according to claim 1, further comprising bringing the nanoparticulate UV protectant together with one or more additives.

12. A process according to claim 11, wherein the one or more additives are one or more of 3-(4'-methylbenzylidene)-dl-camphor, octyl methoxycinnamate, 3,3,5-trimethylcyclohexyl salicylate, 2-ethylhexyl 4-(dimethylamino)benzoate, 2-ethyl-hexyl 2-cyano-3,3-diphenylacrylate, or 2-phenylbenzimidazole-5-sulfonic acid or a potassium, sodium or triethanolamine salt thereof.

13. A process according to claim 11, wherein the one or more additives are one or more cosmetically or dermatologically suitable carriers.

14. A process according to claim 11, wherein the one or more additives are one or more UV filters or self-tanning agents.

15. A process according to claim 1, wherein the hydrothermal treatment is carried out at a temperature of 160° C. to 180° C.

16. A process according to claim 1, wherein the hydrothermal treatment is carried out at a temperature of 180° C.

17. A process according to claim 1, wherein the hydrothermal treatment is carried out at a temperature of 180° C. to 220° C.

18. A process according to claim 1, wherein the hydrothermal treatment is carried out at a temperature of 190° C. to 220° C.

19. A process according to claim 1, wherein the hydrothermal treatment is carried out at a temperature of 150° C. to 210° C.

* * * * *

UNITED STATES PATENT AND TRADEMARK OFFICE
CERTIFICATE OF CORRECTION

PATENT NO. : 8,758,501 B2
APPLICATION NO. : 12/432949
DATED : June 24, 2014
INVENTOR(S) : Pfluecker et al.

It is certified that error appears in the above-identified patent and that said Letters Patent is hereby corrected as shown below:

On the Title Page, Item (63) Related U.S. Application Data reads "Continuation of application No. 10/565,214, filed as application No. PCT/EP2004/007311 on Jan. 20, 2006, now abandoned." should read -- Continuation of application No. 10/565,214, filed Jan. 20, 2006, filed as PCT/EP2004/007311 on Jul. 5, 2004, now abandoned. --

On the Title Page, Item (87) Insert:
-- PCT Pub No.: WO 2005/019348 A1 --
-- PCT Pub Date: March 3, 2005 --

Signed and Sealed this
Seventh Day of April, 2015

Michelle K. Lee
*Director of the United States Patent and Trademark Office*